US007199809B1

(12) United States Patent
Lacy et al.

(10) Patent No.: US 7,199,809 B1
(45) Date of Patent: Apr. 3, 2007

(54) GRAPHIC DESIGN OF COMBINATORIAL MATERIAL LIBRARIES

(75) Inventors: Steven D. Lacy, Sunnyvale, CA (US); Eric W. McFarland, Santa Barbara, CA (US); Adam L. Safir, Berkeley, CA (US); Stephen J. Turner, San Jose, CA (US); Lynn Van Erden, Livermore, CA (US); Pei Wang, San Jose, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

(21) Appl. No.: 09/420,334

(22) Filed: Oct. 18, 1999

Related U.S. Application Data

(63) Continuation-in-part of application No. 09/174,856, filed on Oct. 19, 1998.

(51) Int. Cl.
*G06F 3/00* (2006.01)
*G06F 19/00* (2006.01)

(52) U.S. Cl. .......................................... 345/700; 702/19
(58) Field of Classification Search ................. 345/700, 345/762–764, 781, 810, 835, 839, 853, 866, 345/961, 967, 440, 581, 619; 700/266; 702/22, 702/23, 27, 30, 19, 21; 703/12, 11
See application file for complete search history.

(56) References Cited

U.S. PATENT DOCUMENTS

| 4,422,151 A | 12/1983 | Gilson ......................... 364/496 |
| 4,478,094 A | 10/1984 | Salomaa et al. .............. 73/863 |
| 5,143,854 A | 9/1992 | Pirrung et al. |
| 5,324,483 A | 6/1994 | Cody et al. .................. 422/131 |

(Continued)

FOREIGN PATENT DOCUMENTS

| DE | 29720432 | 5/1999 |
| EP | 0 796 654 A2 | 9/1997 |
| JP | 10-055348 | 2/1998 |
| WO | WO 87/06008 | 10/1987 |
| WO | WO 96/11878 | 4/1996 |
| WO | WO 96/22157 | 7/1996 |
| WO | WO 97/31127 | 8/1997 |
| WO | WO 98/14641 | 4/1998 |
| WO | WO 98/15825 | 4/1998 |
| WO | WO 98/18825 | 4/1998 |
| WO | WO 00/23921 | 4/2000 |

OTHER PUBLICATIONS

Afferent Systems, Inc., "Afferent Analytical ™", pp. 1 of 1, http://www.afferent.com/analytical.html, Copyright© 1996–1999, Last updated Jan. 28, 1999.

Afferent Systems, Inc., "What's new?, IRORI and Afferent enter into Combinatorial Chemistry Collaboration Agreement," pp. 1 of 2, http://www.afferent.com/news.html, Copyright© 1996–1999, Last updated Jul. 3, 1999.

(Continued)

*Primary Examiner*—Crescelle N. dela Torre

(57) ABSTRACT

Computer-implemented methods, programs and apparatus for generating a library design for a combinatorial library of materials. A library design includes a set of sources representing components to be used in preparing the combinatorial library, destinations replying arrangements of cells and mappings, defining one or more distribution patterns for assigning components to cells in the destination arrangement or arrangements. Mappings include gradients and sets of user-defined equations, and are used to calculate the amount of on components to be assigned to a cell or cells in an arrangement. A library design can also include one or more process parameters defined to vary over time or across a plurality of destination cells. The invention outputs a data file defining the library design, including electronic data representing the sources, the destinations and the mapping, in a format suitable for implementing manually or using automated material handling apparatus.

78 Claims, 17 Drawing Sheets

U.S. PATENT DOCUMENTS

| | | | | |
|---|---|---|---|---|
| 5,437,838 | A | | 8/1995 | DeMoranville et al. ........ 422/67 |
| 5,443,791 | A | * | 8/1995 | Cathcart et al. ............ 422/100 |
| 5,463,564 | A | | 10/1995 | Agrafiotis et al. |
| 5,571,639 | A | | 11/1996 | Hubbell et al. |
| 5,574,656 | A | | 11/1996 | Agrafiotis et al. |
| 5,614,608 | A | | 3/1997 | Krchnak et al. ............ 530/334 |
| 5,623,592 | A | * | 4/1997 | Carlson et al. ............. 345/763 |
| 5,714,127 | A | | 2/1998 | DeWitt et al. |
| 5,839,091 | A | * | 11/1998 | Rhett et al. ................... 702/19 |
| 5,856,101 | A | | 1/1999 | Hubbell et al. ................ 435/6 |
| 5,930,154 | A | * | 7/1999 | Thalhammer-Reyero .... 345/764 |
| 5,974,164 | A | | 10/1999 | Chee .......................... 382/129 |
| 6,004,617 | A | * | 12/1999 | Schultz et al. ................ 427/8 |
| 6,044,212 | A | | 3/2000 | Flavin et al. .................. 703/6 |
| 6,045,755 | A | | 4/2000 | Lebl et al. |
| 6,063,339 | A | | 5/2000 | Tisone et al. |
| 6,165,778 | A | * | 12/2000 | Kedar ..................... 435/289.1 |
| 6,175,816 | B1 | | 1/2001 | Flavin et al. ................. 703/13 |
| 6,295,514 | B1 | * | 9/2001 | Agrafiotis et al. ............ 703/12 |
| 6,411,945 | B1 | | 6/2002 | Nakajima ................... 706/19 |
| 6,507,945 | B1 | | 1/2003 | Rust et al. .................. 717/103 |
| 6,618,852 | B1 | | 9/2003 | van Eikeren et al. ....... 717/108 |
| 6,658,429 | B2 | | 12/2003 | Dorsett, Jr. ................. 707/104 |

OTHER PUBLICATIONS

Cargill et al., "Automated Combinatorial Chemistry on Solid Phase", L.R.A., 1996, vol. 8, 139–148.

Advanced Chem. Tech. "Model 496 MOS Multiple Organic Synthesizer", product information, 6 pgs.

Advanced Chem. Tech. "Model 348 MPS Multiple Peptide Synthesizer", product information, 4 pgs, 1997.

The Technology Partnership, "Myriad Personal Synthesis; A New Approach to Synthesis", product information, 7 pgs.

Advanced Chem. Tech. "The ACT Model 90 Tabletop Peptide synthesizer", product information, 2 pgs.

Asymtek "M–MCM".

Asymtek "M–ENCAP", product information, 1 pg.

Asymtek "M–FCOB", product information, 2 pgs.

Bohdan Automation "Solid Phase Extraction Workstation by vacuum".

Carl Crative Systems "Plate Trak Autoamted Liquid Handling System", product information, 1 pg.

Gilson "Better Solutions from Gilson mean . . . ", product information, 1 pg.

HyPrep "ThePrep Plus System", product information, 1 pg.

Packard "Packard . . . The complete solution", product information, 1 pg.

Packard "MuktiPROBE Robotic Liquid Handling Systems" product information, 2 pgs.

Hydra "Pooling Samples, Integrating the Hydra, Dispensing Precision".

Titertek "Quadflex", product information, 2 pgs.

EG&G Wallac MicroBeta "TriLux Scintillation and Luminescence Counter".

Zinsser Analytic "LISSY Pipetting with Windows", product information, 1 pg.

Digitale Mehrkanal–Pipette CALIBRA 852 and DIGIS-CAN, product information, 1 pg.

Automated Organic Synthesis—No Compromises.

Biomek 2000 Laboratory Automation Workstation, product information, 2 pgs.

Chemical Computing Group Inc. "MOE: The Molecular Operating Evironment", product information, 4 pgs. www.chemcomp.com/fdept/prodinfo.htm.

P. Labute, Chemical Computing Group Inc. "MOE: Deployment Strategies", product information, 6 pgs. www.chemcomp.com/feature/deploy.htm.

Afferent Systems, Inc. "Afferent Products" www.afferent.com/products/html, product information, 2 pgs.

Afferent Systems, Inc. "Afferent Defines Libraries In Terms of Precursors and Reactions", product information, 3 pgs., www.afferent.com/products/html.

Afferent Systems, Inc. "Afferent Uses Virtual Chemistry to Generate Combinatorial Products", 6 pgs., www.afferent.com/generation.html.

Afferent Systems, Inc. "The Generic Structure Approach", 3 pgs. www.afferent.com/genric–structure.html.

Afferent Systems, Inc. "Talk Chemistry, Not Robot Language, To Your Synthesis System", 8 pgs. www.afferent.com/control.html.

L. A. Corkan et al., "*Application of an Automated Chemistry Workstation to Problems in Synthetic Chemistry*", Chemometrics and Intelligent Laboratory System: Lab. Info. Mgmt., 1992, vol. 17, pp. 95–105.

L. A. Corkan and J. S. Lindsey, "*Design Concepts for Synthetic Chemistry Workstations*", Advances in Laboratory Automation Robotics, 1990, vol. 6, pp. 447–497.

L. A. Corkan and J. S. Lindsey, "*Experiment Manager Software for an Automated Chemistry Workstation, Including a Scheduler for Parallel Experimentation*", Chemometrics and Intelligent Laboratory Systems; Lab. Info. Mgmt., 1992, vol. 17, pp. 47–74.

J. S. Lindsey, "*Automated Workstations for Chemical Synthesis in Japan: A New Paradigm for Pharmaceutical Research*", Am. Lab., Mar. 1993, pp. 17, 18, 20.

J. S. Lindsey, "*A Retrospective on the Automation of Laboratory Synthetic Chemistry*", Chemometrics and Intelligent Laboratory Systems: Lab. Inf. Mgmt. 1992, vol. 17, pp. 15–45.

J. S. Lindsey and L. A. Corkan, "*Toward High–Performance Parallel Experimentation Machines: Use of a Scheduler as a Quantitative Computer–Aided Design Tool for Evaluating Workstation Performance*", Chemometrics and Intelligent Laboratory Systems: Lab. Info. Mgmt., 1993, vol. 21, pp. 139–150.

J.–C. Plouvier, et al., "*Experiment Planner for Strategic Experimentation with an Automated Chemistry Workstation*", Chemometrics and Intelligent Laboratory Systems: Lab. Info. Mgmt., 1992, vol. 17, pp. 75–94.

Advanced Chem. Tech. "Model 348 MPS Multiple Peptide Synthesizer", product information, 1997, 4 pgs..

Biomek 2000 Laboratory Automation Workstation, product information, 2000, 2 pgs.

Chemical Computing Group Inc. "MOE: The Molecular Operating Environment", product information, 1998, 4 pgs., www.chemcomp.com/fdept/prodinfo.htm.

P. Labute, Chemical Computing Group Inc. "MOE: Deployment Strategies", product information, 1998, 6 pgs., www.chemcomp.com/feature/deploy.htm.

Afferent Systems, Inc. "Afferent Products", product information, 1998, 1 pg., www.afferent.com/products/html.

Afferent Systems, Inc. "Afferent Defines Libraries In Terms of Precursors and Reactions", product information, 1998, 3 pgs., www.afferent.com/libraries.html.

Afferent Systems, Inc. "Afferent Uses Virtual Chemistry to Generate Combinatorial Products", 1998, 6 pgs., www.afferent.com/generation.html.

Afferent Systems, Inc. "The Generic Structure Approach", 1998, 3 pgs. www.afferent.com/genric–structure.html.

Afferent Systems, Inc. "Talk Chemistry, Not Robot Language, To Your Synthesis System", 1998, 8 pgs. www.afferent.com/control.html.

Afferent Systems, Inc., "Afferent Analytical™", p. 1 of 1, http://www.afferent.com/analytical.html., Copyright© 1996–1999, Last updated Jan. 28, 1999.

Afferent Systems, Inc., "What's new?, IRORI and Afferent enter into Combinatorial Chemistry Collaboration Agreement," pp. 1 of 2, http://www.afferent.com/news.html, Copyright© 1996–1999, Last updated Jul. 3, 19993.

X.D. Xiang et al., "A Combinatorial Approach to Materials Discovery", Jun. 23, 1995, Science, vol. 268, pp. 1738–1740.

Robert F. Service, "High–Speed Materials Design", Jul. 25, 1997, Science, vol. 277, pp. 474–475.

B. Jandeleit, et al., "Combinatorial methods in catalysis", Dec. 1998, Baltzer Science Publishers, vol. 2, No. 2, pp. 101–123.

Linda C. Hsieh–Wilson, et al., "Lessons from the Immune System: From Catalysis to Materials Science", © 1996 American Chemical Society, vol. 29m pp. 164–170.

Gabriel Briceño, et al., "A Class of Cobalt Oxide Magnetoresistance Materials Discovered with Combinatorial Synthesis", Oct. 13, 1995, Science, vol. 270, pp. 273–275.

Xiao–Dong Sun, et al., "Indentification and optimization of advanced phosphors using combinatorial libraries", © 1997 American Institute of Physics, vol. 70, No. 25, pp. 3353–3355.

Manfred Beans, et al., "Chemische Reaktionstechnik", 1987, Georg Thieme Veriag, Stuttgart and New york, pp. 226–236 (with English translation).

J.J Hanak, "The "Multiple–Sample Concept" in Materials Research: Synthesis, Compositional Analysis and Testing of Entire Multicomponent Systems", © 1970 Chapman and Hall Ltd., pp. 964–971.

Network Science, "Introducing MDL Screen", download Nov. 15, 2002, <http://netsci.org/Science/Screening/feature03.html>.

Eric W. McFarland and W. Henry Weinberg, "Approaches for Rapid Materials Discovery Using Combinatorial Methods", 1998, Mat. Tech. vol. 13.3, pp. 107–120.

Earl Danielson, et al., "A combinatorial approach to the discovery and optimization of luminescent materials", Oct. 30, 1997, Nature, vol. 389, No. 30, pp. 944–948.

Xiao–Dong Sun, "Solution–Phase Syntheis of Luminescent Materials Libraries", 1997, Advanced Materials, vol. 9, pp. 1046–1049.

Molecular Connection, "MDL's Newsmagazine for Communicating with Customers", Jul. 1998, vol. 17, No. 3, pp. 2–23.

Peter G. Schultz and Xiao–Dong Xiang, "Combinatorial approaches to materials science", 1998, © Current Chemistry ISSN 1359–0286, pp. 153–158.

Statistica vol. IV: Industrial Statistics, Copyright © StatSoft, 1995, pp. 4177–4473.

MDL Screen™ User's Guide, "MDL's Solution for High–Throughput Screening Data Management", © Copyright 1996 by MDL Information Systems, Inc., pp. 1–2 to 14–6.

MODDE 4.0, "Graphical Software for Design of Experiments", © 1992–1997 Umetri AB, pp. 1–1 to 41–2.

H.–D. Klein, "Statistische Versuchsplanung", 1995, Nachr. Chem. Tech. Lab. vol. 43, pp. 1078, 1080–1082 (with English translation).

Kagaku, "Combinatorial Chemistry: Inconceivable without Computers", *Combinatorial Chemistry*, vol. 51, No. 8, pp. 480–483 & 583 (1996). Orginal Japanese reference and English translation included.

Yamagata et al., "Constructing an Assay System with HTS", *IV High Throughput Screening*, pp. 179–191 (1997). Original Japanese reference and English translation included.

MultiPROBE® II Automated Liquid Handling System, Operation Manual, Packard Instrument Company, Inc. 1998.

Eclipse 4000 User Software for the MICROLAB® 4000 Series Version 1.1 User's Manual, Hamilton Company 1998.

Jandeleit et al., *Angew. Chem.* 1999, 38, 2494–2532.

MICROLAB® 4000 Robotic Workstations, Hamilton Company 1999.

Microlab AT plus 2, Sunrise Plus Version 3.3 Software Instructions, Hamilton Bonaduz AG, 1996.

MultiPROBE® II Automated Liquid Hangling System, Operation Manual, Packard Instrument Company, 1999.

MultiPROBE® II Automated Liquid Handling System, Operation Manual, Packard Instrument Company, 1996.

MultiPROBE® II Automated Liquid Handling Systems, Specifications, Packard Instrument Company, 1998.

PAL Cycle Composer User Manual, CTC Analytics AG, Sep. 1998.

TECAN Facts Software Manual, Tecan AG, V1.0, Nov. 1998.

Tecan Gemini Software Manual, Tecan AG, V2.0, Aug. 1998.

EPO Communication re Application No. / Patent No.: 99955064.3–2201/1080435 mailed Dec. 20, 2004 (27 pages).

EPO Communication re Application No. / Patent No.: 99955064.3–2201/0180435 mailed Feb. 25, 2005 (8 pages).

EPO Opposition Document filed by Degussa on May 5, 2003, re EP Patent 1 080 435 B1. Original German reference and English translation included (4 pages).

* cited by examiner

| Seq # | Source | Destination | Amount | To Recipe | Tag |
|---|---|---|---|---|---|
| 1 | F (1,1),(1,1) | Plate (1,1),(7,4) | 10.00 to 70.00 | ✓ | |
| 2 | E (1,1),(1,1) | Plate (1,5),(7,8) | 10.00 to 70.00 | ✓ | |
| 3 | G (1,1),(1,1) | Plate (1,9),(7,12) | 10.00 to 70.00 | ✓ | |
| 4 | B (1,1),(1,1) | Plate (1,1),(2,4) | 10.00 to 40.00 | ✓ | |
| 5 | B (1,1),(1,1) | Plate (1,5),(2,8) | 10.00 to 40.00 | ✓ | |
| 6 | B (1,1),(1,1) | Plate (1,9),(2,12) | 10.00 to 40.00 | ✓ | |
| 7 | C (1,1),(1,1) | Plate (5,1),(6,4) | 10.00 to 40.00 | ✓ | |
| 8 | C (1,1),(1,1) | Plate (5,5),(6,8) | 10.00 to 40.00 | ✓ | |
| 9 | C (1,1),(1,1) | Plate (5,9),(6,12) | 10.00 to 40.00 | ✓ | |
| 10 | B (1,1),(1,1) | Plate (8,1),(8,2) | 70.00 to 70.00 | ✓ | |
| 11 | C (1,1),(1,1) | Plate (8,9),(8,10) | 70.00 to 70.00 | ✓ | |
| 12 | H (1,1),(1,1) | Plate (1,1),(8,12) | 500.00 to 500.0 | ✓ | |
| 13 | A (1,1),(1,1) | Plate (3,1),(4,4) | 10.00 to 40.00 | ✓ | |

| Destination (1, 1) | | | | | | |
|---|---|---|---|---|---|---|
| Source | | Chemicals | | | | |
| Name | Amount (uL) | Name | uMole | Mole Fraction | Mass (mg) | Mass Fraction |
| SubB | 109.1 | A | 3200.00000 | 0.98323 | 80.00000 | 0.87993 |
| SolvA | 690.4 | B | 54.55010 | 0.01676 | 10.91002 | 0.12000 |
| CoCatE | 0.0 | D | 0.00546 | 0.00000 | 0.00546 | 0.00006 |
| CatD | 0.5 | E | 0.00055 | 0.00000 | 0.00027 | 0.00000 |
| | | K | 0.01091 | 0.00000 | 0.00109 | 0.00001 |

GRAPHIC DESIGN OF COMBINATORIAL MATERIAL LIBRARIES

CROSS REFERENCE TO RELATED APPLICATIONS

This is a continuation-in-part of U.S. Ser. No. 09/174,856, filed Oct. 19, 1998, which is incorporated by reference in its entirety and which is the basis of a claim of priority under 35 U.S.C. § 120.

BACKGROUND OF THE INVENTION

The present invention relates to the computer-implemented design of combinatorial libraries of materials. Traditionally, the discovery and development of materials has predominantly been a trial and error process carried out by scientists who generate data one experiment at a time. This process suffers from low success rates, long time lines, and high costs, particularly as the desired materials increase in complexity. When a material is composed of multiple components, theory provides little guidance, and the large variety of possible combinations of components takes a large amount of time to prepare and analyze.

Combinatorial materials science addresses some of these challenges. Combinatorial materials science refers generally to methods for creating collections or libraries of chemically diverse compounds or materials and/or to methods for rapidly testing or screening these libraries for compounds or materials having desirable performance characteristics and properties. By parallel or rapid serial testing of many compounds or materials, combinatorial techniques accelerate the speed of research, facilitate breakthroughs, and expand the amount of information available to researchers. Furthermore, the ability to observe the relationships between hundreds or thousands of materials in a short period of time enables scientists to make well-informed decisions in the discovery process and to find unexpected trends.

Researchers employing combinatorial techniques design libraries or arrays containing multiple combinations of starting chemicals. It is desirable to design such libraries to explore a desired phase space of starting components and realize good experimental results at a reasonable cost and period of time. Computer programs have been used for life science libraries, and some software applications have been applied to materials. Many of these programs allow for step-by-step input of a detailed protocol for synthesizing a library of materials, but do not allow for definition of chemical ratios or process parameters. To implement such protocols, the user must manually determine the proper concentration and quantity of each starting material to achieve a desired ratio of starting materials in each library member. For large libraries with shared starting solutions, this becomes unwieldy to solve manually without significantly limiting the diversity studied within one library. Other programs allow for definition of chemical ratios or process parameters to apply to a whole library, by do not provide for high level definition of multi-dimensional variation of these ratios or parameters across the spatial dimensions of the library, also limiting the diversity that may be studied within a single library. Some of these programs have been either spreadsheet based or graphic-based. Spreadsheet-like interfaces are, for many users, non-intuitive and difficult to learn. Graphic-based interfaces are somewhat more intuitive, but are limited to supplying direct machine instructions to move volumes of liquid on a specific robotic system. Such interfaces fail to provide the comprehensive conceptual library design assistance that materials discovery chemists would find greatly beneficial. Many a existing programs are limited to specific chemistries, such as those used in the pharmaceutical industry, and can only interface with a specific type of synthesis instrument.

SUMMARY OF THE INVENTION

The invention provides computer implemented methods and apparatus for designing combinatorial libraries of materials. The invention provides a graphical user interface through which the user designs a library conceptually, with the ability to specify the desired material composition of multiple library members in terms of a variety of interrelationships between component materials, such as multiple interdependent gradients or ratios of component materials. The resulting conceptual library design is not constrained by the physical limitations of available library substrates or equipment. The invention's graphical interface allows the user to define variation of chemical ratios or process parameters across a library or across one or more distinct, partially intersecting or completely overlapping sub-regions of the library. The invention receives the user's conceptual design and performs the detailed calculations necessary to determine the precise composition of each member of the library. The invention outputs a data file in a format suitable for manual library preparation or automated preparation using conventional material handling apparatus. The output may include a list of mappings to be performed in preparing a library.

In general, in one aspect, the invention features a computer-implemented method for generating a library design for a combinatorial library of materials. The method includes defining one or more sources and one or more destinations, receiving an input defining a first mapping, using the first mapping to calculate a composition of one or materials assigned to one or more of cells of the destination, and generating a data file defining the library design.

Each source is electronic data representing a component to be used in preparing the combinatorial library. Each destination is electronic data representing an arrangement of cells. The first mapping is electronic data defining a distribution pattern for assigning a component to cells in the arrangement. The distribution pattern includes a minimum and a maximum amount of the component to be assigned to any cell of the arrangement and a gradient to be applied between the minimum and maximum amounts of the component across the cells. The data file includes electronic data representing the sources, the destinations and the mapping.

Implementations of the invention can include one or more of the following advantageous features. The method includes displaying a representation of the library design graphically describing the composition of one or more materials assigned to one or more of the cells. The data file includes electronic data representing one or more sets of properties, each set of properties being associated with one of the sources, the destinations or the mapping. Defining the sources and destinations includes receiving an input from a graphical input device. The input defining a first mapping includes a selection from a set of available mapping types, including a one to one mapping of a component from a source to a cell in the arrangement and a one to many mapping of a component from a source to a plurality of cells in the arrangement. The set of available mapping types also includes a many to many mapping of a plurality of components from a plurality of sources to a plurality of cells in the arrangement, a many to one mapping of a plurality of components from a plurality of sources to a cell in the arrangement, or a set of one or more user-defined equations. The gradient is selected from the group consisting of linear, logarithmic, exponential, polynomial and geometric progression. The set of properties associated with the mapping includes a source name, a source geometry, a destination name, a destination geometry, a gradient type, and a set of gradient parameters defining the gradient. The method includes receiving an input defining a second mapping, and using the first and second mappings to calculate a composition of one or more materials assigned to one or more of the cells. The second mapping is electronic data defining a second distribution pattern for distributing a second component to cells in the arrangement. The second distribution pattern includes electronic data identifying a fixed amount of the second component to be assigned to one or more cells in the arrangement. The second distribution pattern includes electronic data identifying a minimum and a maximum amount of the second component to be assigned to any of the cells of the arrangement and a second gradient to be applied between the minimum and maximum amounts of the second component across the cells. The method includes generating a modified library design by receiving an input redefining a source, a destination or a mapping, recalculating the composition of one or more materials assigned to one or more of the cells; and generating a data file defining the modified library design. The method includes receiving an input defining one or more parameters, and the data file includes electronic data representing the one or more parameters. Each parameter is electronic data corresponding to a process parameter and defines a parameter value for one or more cells of the arrangement. The parameter values vary between a minimum and a maximum amount. The arrangement comprises two or more cells, ten or more cells, or about ninety-six or more cells.

In general, in another aspect, the invention features a computer-implemented method for generating a library design for a combinatorial library of materials. The method includes defining a set of one or more sources and one or more destinations, receiving an input defining a set of first mappings, using the set of equations to calculate a composition of a material assigned to one or more cells in the destination, and generating a data file defining the library design. Each source is electronic data representing a component to be used in preparing the combinatorial library. Each destination is electronic data representing an arrangement of cells. The set of first mappings is electronic data defining a set of equations for calculating an amount of one or more components to be assigned to one or more cells in the destination arrangement. The data file includes electronic data representing the sources, the destinations and the mappings.

Implementations of the invention can include one or more of the following advantageous features. The method includes displaying a representation of the library design. The representation graphically describes the composition of one or more materials assigned to one or more of the cells. The component to be assigned to a cell in the arrangement is determined by the location of the cell within the arrangement. The composition of a material is determined using a subset of the set of equations, the subset of equations being determined by the location of the cell within the arrangement. The method includes generating an error indicator signal if the number of equations in the set of equations is not equal to the number of sources in the set of sources. At least one of the set of equations is selected from a ratio equation defining an amount of a component to be assigned to a cell as a function of an amount of another component to be assigned to the cell; a volume equation defining an amount of a component to be assigned to a cell as a function of a total volume of a plurality of components to be assigned to the cell; and a mass equation defining an amount of a component to be assigned to a cell as a function of a total mass of a plurality of components to be assigned to the cell. The set of equations includes a gradient equation defining an amount of a component to be assigned to each of a plurality of cells according to a gradient. Each of the set of equations is assigned to one or more cells of the arrangement according to the location of the cells within the arrangement. The method includes simultaneously solving a set of interdependent equations. The method includes using a matrix inversion technique to solve the set of equations. The method includes receiving an input defining a second mapping and using the first set of mappings and the second mapping to calculate a composition of a material assigned to one or more of the cells. The second mapping is electronic data defining a distribution pattern for distributing a component to cells in the arrangement. The distribution pattern includes a minimum and a maximum amount of the component to be assigned to any cell of the cells of the arrangement and a gradient to be applied between the minimum and maximum amounts of the component across the plurality of cells.

In general, in another aspect, the invention features a computer-implemented method for generating a library design for a combinatorial library of materials. The method includes defining a set of one or more sources and one or more destinations, defining a plurality of mappings, receiving an input defining one or more parameters, and generating a data file defining the library design. Each source is electronic data representing a component to be used in preparing the combinatorial library. Each destination is electronic data representing an arrangement of cells. The mappings in the aggregate define a composition for each of a plurality of materials assigned to a plurality of cells in the arrangement. Each parameter is electronic data corresponding to a process parameter and defining a parameter value for one or more cells of the arrangement. The parameter value varies between a minimum and a maximum amount. The data file includes electronic data describing the source elements, the destination elements, the mappings and the parameters.

Implementations of the invention can include one or more of the following advantageous features. The parameter value is defined to vary over time, across two or more cells in the arrangement, or over time and across two or more cells in the arrangement. The parameter value varies according to a gradient selected from the group consisting of linear, logarithmic, exponential, polynomial and geometric progression. The parameter value corresponds to a process parameter selected from the group consisting of temperature, pressure, time, flow rate and stirring speed.

In general, in another embodiment, the invention features a computer-implemented method for preparing a combinatorial library of materials on a substrate. The method includes creating a library design by defining a set of design elements, generating a data file comprising electronic data describing the set of design elements, and using the data file to cause an automated material handling apparatus to assemble the combinatorial library on a substrate. The set of design elements includes one or more sources representing components to be used in preparing the combinatorial library, one or more destinations, each of which includes an arrangement of one or more cells, and one or more elements selected from the group consisting of a mapping defining a scheme for assigning one or more amounts of a component to one or more cells of an arrangement and a parameter corresponding to a process parameter. The parameter defines a parameter value for one or more cells of the arrangement. The parameter value varies between a minimum and a maximum amount.

In general, in another embodiment, the invention features a computer program product on a computer-readable medium for generating a library design for a combinatorial library of materials. The computer program includes instructions operable to cause a programmable processor to receive an input defining one or more sources and one or more destinations, receive an input defining a first mapping, use the first mapping to calculate a composition of one or materials assigned to one or more cells in the destination, and generate a data file defining the library design. Each source is electronic data representing a component to be used in preparing the combinatorial library. Each destination is electronic data representing an arrangement of cells. The first mapping is electronic data defining a distribution pattern for assigning a component to cells in the arrangement. The distribution pattern includes a minimum and a maximum amount of the component to be assigned to any cell of the arrangement and a gradient to be applied between the minimum and maximum amounts of the component across the plurality of cells. The data file includes electronic data representing the sources, the destinations and the mapping.

Implementations of the invention can include one or more of the following advantageous features. The computer program includes instructions operable to cause a programmable processor to display a representation of the library design graphically describing the composition of one or more materials assigned to one or more of the cells.

The data file includes electronic data representing one or more sets of properties, each set of properties being associated with one of the sources, the destinations or the mapping. The input defining the sources and destinations includes an input from a graphical input device. The input defining a first mapping includes a selection from a set of available mapping types. The set of available mapping types includes a one to one mapping of a component from a source to a cell in the arrangement and a one to many mapping of a component from a source to a plurality of cells in the arrangement, a many to many mapping of a plurality of components from a plurality of sources to a plurality of cells in the arrangement, a many to one mapping of a plurality of components from a plurality of sources to a cell in the arrangement, or a set of one or more user-defined equations. The gradient is selected from the group consisting of linear, logarithmic, exponential, polynomial and geometric progression. The set of properties associated with the mapping comprises a source name, a source geometry, a destination name, a destination geometry, a gradient type, and a set of gradient parameters defining the gradient. The computer program includes instructions operable to cause a programmable processor to receive an input defining a second mapping and use the first and second mappings to calculate a composition of one or more materials assigned to one or more of the cells. The second mapping is electronic data defining a second distribution pattern for distributing a second component to cells in the arrangement. The second distribution pattern includes electronic data identifying a fixed amount of the second component to be assigned to one or more cells in the arrangement. The second distribution pattern includes electronic data identifying a minimum and a maximum amount of the second component to be assigned to any of the cells of the arrangement and a second gradient to be applied between the minimum and maximum amounts of the second component across the cells. The computer program includes instructions operable to cause a programmable processor to generate a modified library design by receiving an input redefining a source, a destination or a mapping; recalculating the composition of one or more materials assigned to one or more of the cells; and generating a data file defining the modified library design. The computer program includes instructions operable to cause a programmable processor to receive an input defining one or more parameters and the data file includes comprises electronic data representing the one or more parameters. Each parameter is electronic data corresponding to a process parameter and defining a parameter value for one or more cells of the arrangement. The parameter value varies between a minimum and a maximum amount. The arrangement comprises two or more cells, ten or more cells, or about ninety-six or more cells.

In general, in another embodiment, the invention features a computer program product on a computer-readable medium for generating a library design for a combinatorial library of materials. The computer program includes instructions operable to cause a programmable processor to receive an input defining a set of one or more sources and one or more destinations, receive an input defining a set of first mappings, use the set of equations to calculate a composition of a material assigned to one or more of cells of the destination, and generate a data file defining the library design. Each source is electronic data representing a component to be used in preparing the combinatorial library. Each destination is electronic data representing an arrangement of cells. The set of first mappings is electronic data defining a set of equations for calculating an amount of one or more components to be assigned to one or more cells in an arrangement. The data file includes electronic data representing the sources, the destinations and the mappings.

Implementations of the invention can include one or more of the following advantageous features. The computer program includes instructions operable to display a representation of the library design graphically describing the composition of one or more materials assigned to one or more of the cells. The component to be assigned to a cell in the arrangement is determined by the location of the cell within the arrangement. The composition of a material is determined using a subset of equations determined by the location of the cell within the arrangement. The computer program includes instructions operable to generate an error indicator signal if the number of equations in the set of equations is not equal to the number of sources in the set of sources. At least one of the set of equations is selected from a ratio equation defining an amount of a component to be assigned to a cell as a function of an amount of another component to be assigned to the cell, a volume equation defining an amount of a component to be assigned to a cell as a function of a total volume of a plurality of components to be assigned to the cell, and a mass equation defining an amount of a component to be assigned to a cell as a function of a total mass of a plurality of components to be assigned to the cell. The set of equations includes a gradient equation defining an amount of a component to be assigned to each of a plurality of cells according to a gradient. The set of equations is assigned to one or more cells of the arrangement according to the location of the cells within the arrangement. The instructions operable to cause a programmable processor to use the set of equations to calculate a composition of a material assigned to one or more of the cells include instructions simultaneously to solve a set of interdependent equations. The instructions simultaneously to solve the set of interdependent equations include instructions to use a matrix inversion technique to solve the set of equations. The computer program includes instructions operable to receive an input defining a second mapping and use the first set of mappings and the second mapping to calculate a composition of a material assigned to one or more of the cells. The second mapping is electronic data defining a distribution pattern for distributing a component to cells in the arrangement. The distribution pattern includes a minimum and a maximum amount of the component to be assigned to any cell of the cells of the arrangement and a gradient to be applied between the minimum and maximum amounts of the component across the plurality of cells.

In general, in another embodiment, the invention features a computer program product on a computer-readable medium for generating a library design for a combinatorial library of materials. The computer program includes instructions operable to cause a programmable processor to receive an input defining a set of one or more sources and one or more destinations, receive an input defining a plurality of mappings, receive an input defining one or more parameters, and generate a data file defining the library design. Each source is electronic data representing a component to be used in preparing the combinatorial library. Each destination is electronic data representing an arrangement of cells. The mappings in the aggregate define a composition for each of a plurality of materials assigned to a plurality of cells in the arrangement. Each parameter is electronic data corresponding to a process parameter and defining a parameter value for one or more cells of the arrangement. The parameter value varies between a minimum and a maximum amount. The data file includes electronic data describing the source elements, the destination elements, the mappings and the parameters.

Implementations of the invention can include one or more of the following advantageous features. The parameter value is defined to vary over time, across two or more cells in the arrangement, or over time and across two or more cells in the arrangement. The parameter value varies according to a gradient selected from the group consisting of linear, logarithmic, exponential, polynomial and geometric progression. The parameter value corresponds to a process parameter selected from the group consisting of temperature, pressure, time, flow rate and stirring speed.

In general, in another aspect, the invention features a computer program product on a computer-readable medium for generating a library design for a combinatorial library of materials. The computer program includes instructions operable to cause a programmable processor to create a library design by defining a set of design elements, generate a data file including electronic data describing the design and use the data file to cause an automated material handling apparatus to assemble the combinatorial library on a substrate. The set of design elements includes one or more sources representing components to be used in preparing the combinatorial library, one or more destinations, and one or more elements selected from the group consisting of a mapping defining a scheme for assigning one or more amounts of a component to one or more cells of an arrangement and a parameter corresponding to a process parameter. Each destination includes an arrangement of one or more cells. The parameter defines a parameter value for one or more cells of the arrangement, the parameter value varying between a minimum and a maximum amount.

Advantages that can be seen in implementations of the invention include one or more of the following. The invention allows users to design combinatorial libraries conceptually, while automatically performing a large number of detailed calculations required for the exact assignment of materials at each library member in a process that is preferably invisible to the user, although it may be shown if desired. The user can visualize a conceptual library design and identify potential errors before undertaking actual library synthesis. Separation of library design from library synthesis allows the user to lay out a library design conceptually, without regard for the physical limitations of a particular destination substrate or synthesis apparatus. The library design can flexibly define variation of chemical composition across library members by specifying multiple, interdependent material gradients or ratios defining the composition of each library member. The library design can also include variation of process parameters over time or across library members, which enables the user combinatorially to explore the effect of changing process conditions on material composition. The output of the design process is a recipe file that allows the automated synthesis of a library corresponding to the conceptual design. Maintaining databases of chemical information, library designs and composition data speeds up library design, avoids the repetition of old experiments, and assists in the overall planning and execution of experiments necessary to explore the preparation and properties of diverse materials.

The details of one or more embodiments of the invention are set forth in the accompanying drawings and the description below. Other features and advantages of the invention will become apparent from the description, the drawings, and the claims.

BRIEF DESCRIPTION OF THE DRAWINGS

FIG. 6C is an example of a mapping dialog displaying a sequence of defined mappings defining a library.

FIG. 8D is an example of a dialog depicting the composition of a library member.

Like reference numbers and designations in the various drawings indicate like elements.

DETAILED DESCRIPTION

Figure 1:
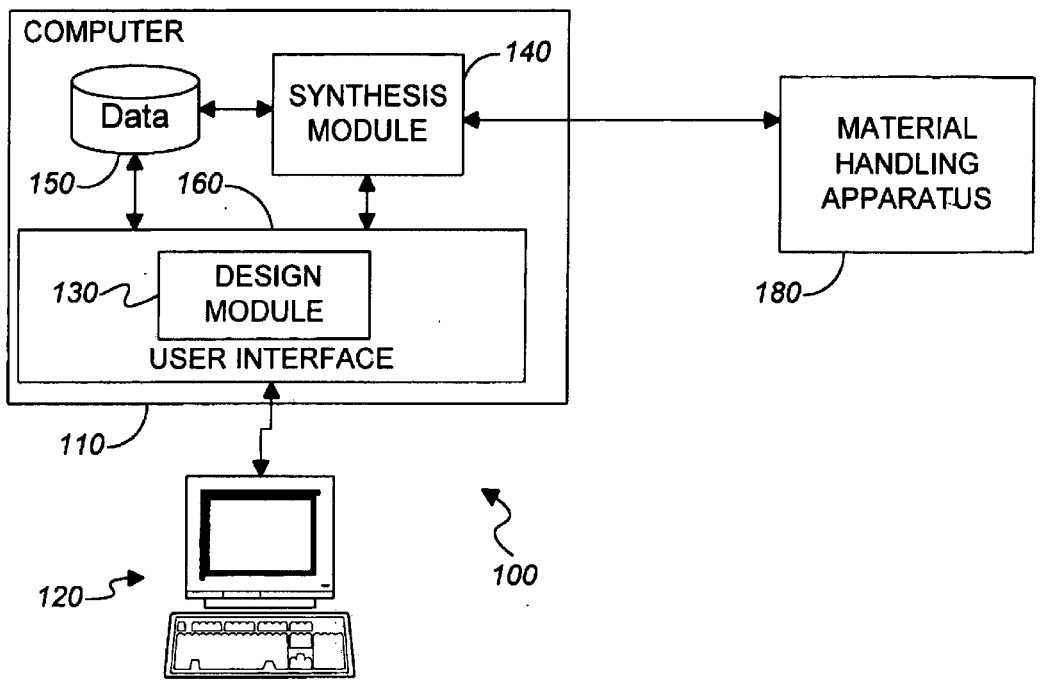
FIG. 1 is a block diagram illustrating a system for computer-implemented design of a combinatorial library of materials.
Figure 2:
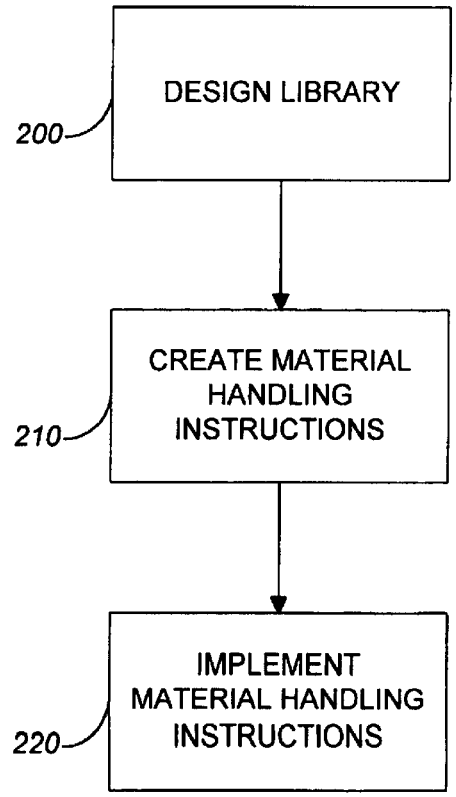
FIG. 2 is a flow diagram generally illustrating a method of designing a combinatorial library of materials.

As shown in FIGS. 1 and 2, a system 100 includes a computer 110 equipped with input/output devices 120. A typical user of system 100 is a chemist. Through user interface 160, the user initializes system 100 and generates a library design for a combinatorial library of materials using design module 130 (step 200). As used in this specification, a combinatorial library is a collection of two or more members that contain some variance in chemical composition, chemical amount, reaction conditions, and/or processing conditions, where a member is a single position in a library containing one set of chemicals subject to one set of reaction or processing conditions.

Based on the library design, design module 130 creates a set of material handling instructions, which may take the form of a data file or "recipe file" (step 210), which may be provided to synthesis module 140 (step 220). Synthesis module 140 implements the instructions, by causing material handling apparatus 180 to synthesize a combinatorial library specified by the design, for example (step 230). Implementation of material handling instructions from recipe files to synthesize libraries of materials is described in more detail in U.S. application Ser. No. 09/305,830, filed on May 5, 1999, which is incorporated herein by reference in its entirety. Alternatively, design module 130 stores the set of material handling instructions in a file or relational database in memory 150 for later modification by design module 130 or implementation by synthesis module 140.

Figure 3:
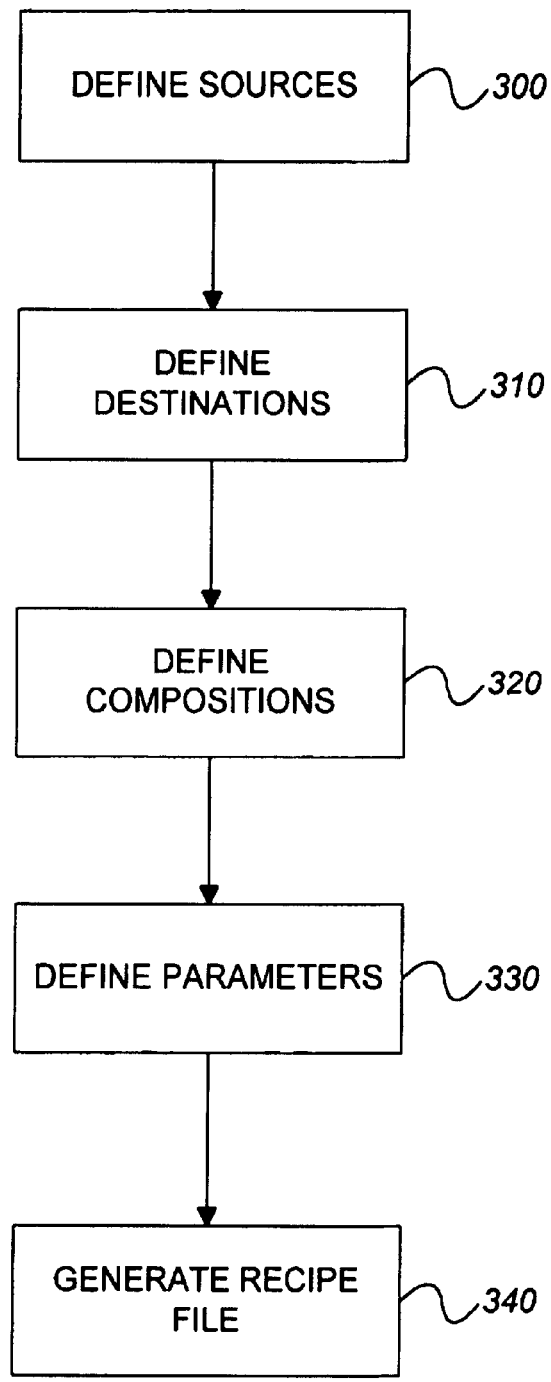
FIG. 3 is a flow diagram illustrating a method of designing a combinatorial library of materials.
Figure 4:
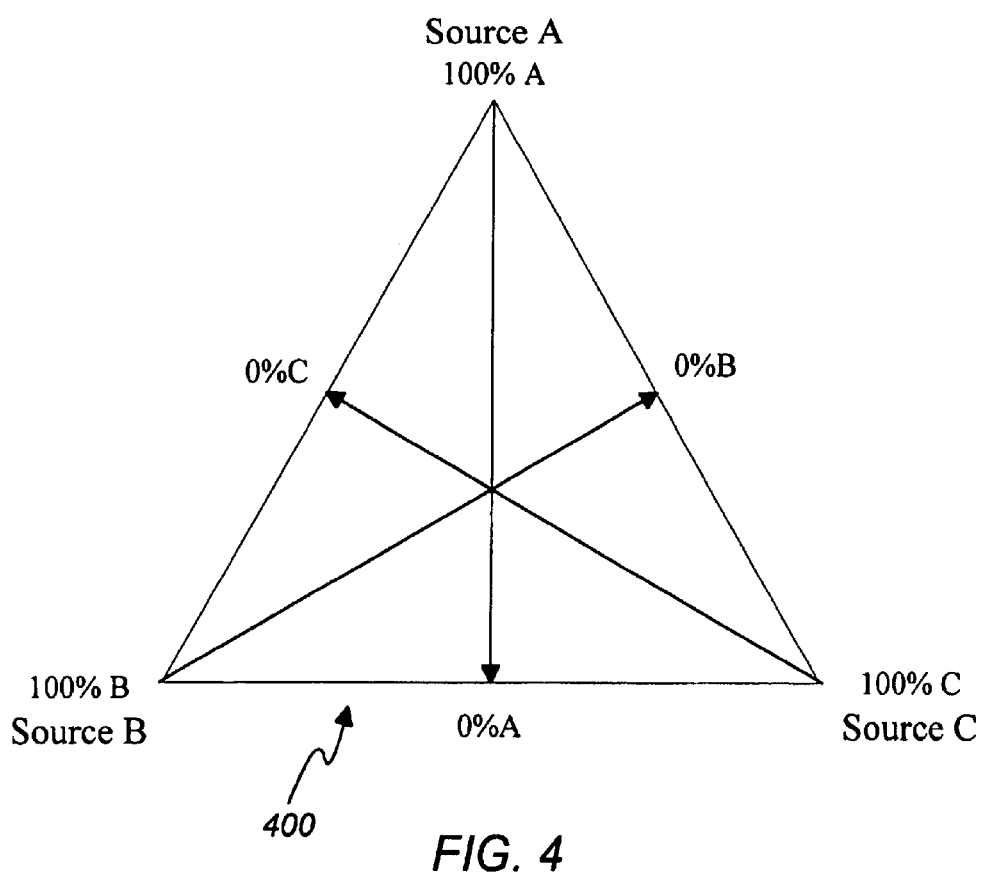
FIG. 4 is a ternary phase diagram describing the design of a conceptual triangular library of cells containing a mixture of three components in varying degrees.

Using design module 130, the user designs a library by defining a set of design elements corresponding to a design workspace, one or more mappings or distribution schemes for assigning materials to individual library members, and, optionally, one or more process parameters to be applied to one or more library members. FIG. 3 shows a method of using system 100 to design a combinatorial library of materials in more detail. Through user interface 160, the user defines a workspace by defining one or more sources (step 300) and one or more destinations (step 310). As used in this specification, a source is a chemical or mixture of chemicals that will be used as a component in creating a library, while a destination is a conceptual arrangement of cells representing a combinatorial library. In one embodiment, a destination may represent a physical substrate in or on which a library is created. In other embodiments, however, a destination is not constrained to represent an actual physical substrate, but can correspond to a conceptual library environment. Thus, as shown in FIG. 4 for example, a user may design a ternary library of three components A, B and C on a triangular destination in which each apex of triangle 400 corresponds to a composition of 100 percent of the corresponding component, while design module 130 translates the triangular conceptual design to a conventional rectangular grid corresponding to locations on a wafer or wells in a micrometer plate, as will be described in more detail below. The user defines each source and destination by entering identifying information, which may cause design module 130 to create a corresponding source or destination data object having associated properties defined by the user input, as will be described in more detail below. Alternatively, the user defines a source or destination by retrieving a pre-defined source or destination from memory 150.

The definition of sources and destinations is described in more detail with reference to FIGS. 5A–C. The user defines the necessary sources (meaning components to be used in designing and synthesizing a library, which may include materials located at one or more destination regions as will be. Described below) and destinations using design window 500, which includes outline pane 510, definition pane 530 and graphical pane 540. Outline pane 510 depicts a hierarchical view of the library design and its contents. At the top level, outline pane 510 displays a list of library design folders 511, each containing a library design. The next level lists sub-folders corresponding to the contents of each design, including, for example, sources folder 512, destinations folder 513, chemicals folder 514, equations folder 515 and parameters folder 516. At the third level, outline pane 510 displays icons depicting the individual design elements, including, for example, sources 517, destinations 518, chemicals 519, equations and parameters. When the user selects an icon corresponding to a desired element, user interface 160 displays information relevant to that element—for example, selection of a source 517 may result in display of a dialog identifying the names of the source's constituent chemicals, or other relevant properties. The hierarchical view in outline pane 510 also includes an icon 520 representing a recipe file corresponding to the library design.

The user defines a set of sources (such as stock solutions containing one or more chemicals dissolved in a solvent) to be used in creating the library, by, for example, selecting "Stock Materials" tab 525 (or a corresponding button on toolbar 560, a menu item in menus 570 or the like), which causes definition pane 530 to display a stock materials layer. Appropriate source materials (i.e., components for use in library design) can include chemical elements, chemical compounds or chemical compositions, which may themselves include one or more elements or compounds. Source materials can be in a gaseous, liquid or solid phase.

For each source material, the user assigns a source name in field 531, and may enter information defining the source properties, including attributes of each constituent chemical such as type (or subtype), name (selected, for example, from a list of defined chemicals), molecular weight, equivalents, structure, density and concentration into corresponding fields 532–539. Values corresponding to source properties may be entered in any convenient units and are converted to common units for subsequent calculations by design module 130. To facilitate graphic display, each source may be assigned a distinct color. As sources are defined, they are depicted as source icons 517 in sources folder 512 in outline pane 510.

Each source is also represented by an icon or shape 541 in graphical pane 540, which may be manipulated by the user—for example, by using a mouse or other input device to move or drag the icon to any desired location in graphical pane 540 or to resize the icon as desired.

Figure 5A:
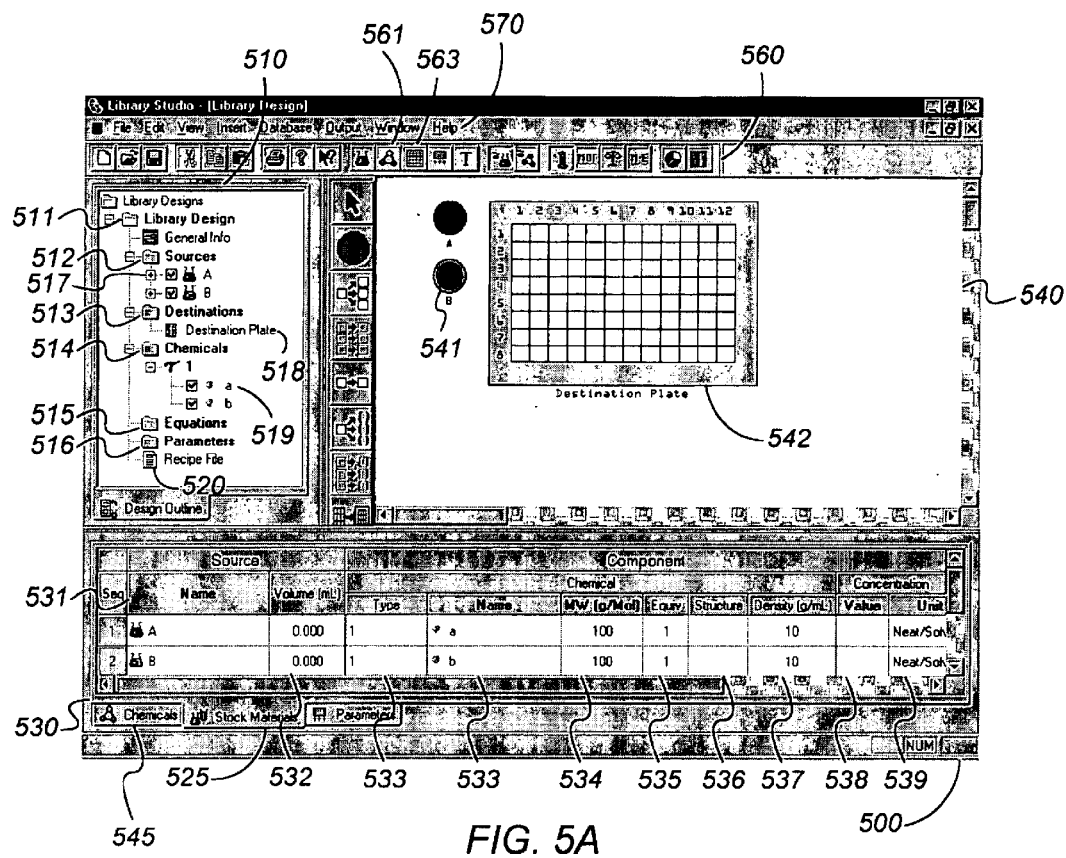
FIG. 5A is a user interface window for use by a user designing a combinatorial library of materials.
Figures 5B, 5C:
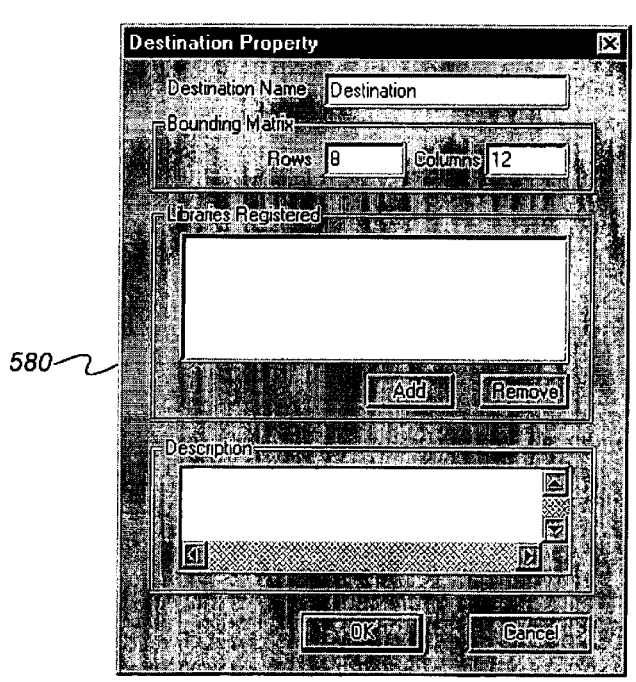
FIG. 5B is an example of a window pane of the system user interface for defining one or more stock materials.
FIG. 5C is an example of a dialog of the system user interface for defining a destination object.

To define a chemical (a single material component within a synthetic design, for example a reagent that is synthesized or purchased for use in a source), the user makes an appropriate selection, such as by selecting "Chemicals" tab 545 in layered definition pane 530, causing that pane to toggle to a chemical definition layer 550, as shown in FIG. 5B. Alternatively, the user selects New Chemical button 561 on toolbar 560, an appropriate entry from drop-down menus 570, or other selection device. The user enters the chemical's name into Chemical Name field 552 and enters information defining the chemical's properties, such as molecular weight, equivalents, structure and density, into corresponding fields 553, 554, 555 and 556. Optionally, the user also assigns a chemical "Type"—a user-selected label describing a class of chemicals that may be used as a design parameter in creating the library—by entering a name into Type field 551. Each defined chemical type may include one or more subtypes. Alternatively, the user may retrieve the relevant data for a pre-defined chemical or chemicals from a database in memory 150 and transfer the data directly into the corresponding fields of the chemical definition layer.

To facilitate implementation of a library design, in one embodiment design module 130 outputs a stock solution preparation worksheet that can be used for the manual or automated preparation of actual stock solutions to be used to synthesize the library. After the stock solutions are prepared, the user may enter actual values for mass, volume and concentrations of stock solution components, enabling design module 130 to recalculate its usage of stock materials based on the actual composition of available stock solutions.

The user defines one or more destinations by selecting an appropriate button or menu item, such as New Destination button 563 on toolbar 560, and entering a destination name and geometry information. Each destination includes one or more regions, each of which may be represented as a cell or group of cells in an arrangement (e.g., an array) of one or more cells. A destination can include an arrangement of two or more cells, preferably four, ten, twenty, or even ninety-six or more cells. The cells or regions of a destination may, but need not, correspond to members of the combinatorial library and/or locations on a physical substrate (such as a micrometer plate, wafer or the like) on which the library will be created. However, while the destination may correspond to the geometry of the ultimate physical substrate, it may also represent the library on a more conceptual level, and may correspond to an abstract intermediate in the ultimate library design as will be described in more detail below. A destination can encompass one or more library designs; conversely, a library design can encompass any number of regions or cells of a destination, from a single cell to the total number of cells associated with the destination. In the described embodiment, destinations are depicted as square or rectangular arrays. However, destinations and the libraries they represent may be designed in any convenient shape, such as square, rectangle, circle, triangle or the like. Selection of a desired arrangement is a choice that can be manipulated by this invention. Strategies for designing combinatorial libraries are described in U.S. application Ser. No. 09/156,827, filed Sep. 18, 1998, and U.S. Pat. No. 5,776,359, both of which are incorporated herein by reference.

Thus, the user defines a destination by, for example, entering a number of rows and columns defining a bounding matrix of the destination into fields 581 and 582 of Destination Property dialog 580 shown in FIG. 5C. Each defined destination is represented as destination icons 517 in destinations folder 513 and as an appropriately-sized empty arrangement 542 of the appropriate shape in graphical pane 550, which may be manipulated by the user, such as by dragging to desired locations in graphical pane 550 or by resizing, as described for sources above.

Referring again to FIG. 3, the user designs the combinatorial library by assigning components (including chemicals) from sources to destination regions to define the composition of each library member (step 320). In one embodiment, described in detail with reference to FIGS. 6A–6C, the user directly defines one or more mappings that represent the assignment of one or more components to one or more destination cells. After defining the necessary sources and destination, represented as circles 601–603 and arrangement 607, respectively, in graphical pane 600, the user designs the library by using toolbar 610 to define a sequence of one or more mappings, each of which embodies a scheme or pattern for assigning an amount of a component or components from a source or sources to a destination region (i.e., a cell or group of cells), or from a destination region to one or more other cells of the same or a different destination. As described below, mappings can be defined from a single source to a single destination region, from one source to multiple destination regions or from multiple sources (or destination regions) to multiple destination regions. The user may define a mapping by specifying that one or more components are to be assigned to one or more destination regions in uniform amounts or in varying amounts defined by a mathematical gradient or by a set of one or more governing equations applied to one or more destination regions, or by some combination of these methods.

To define a mapping, the user selects a mapping mode by, for example, selecting the appropriate button in toolbar 610. In one embodiment, to define a "one-to-one" mapping assigning a single component to a single destination cell the user selects one-to-one mapping button 615. The user then selects a desired source, for example by highlighting an icon or shape in graphical pane 600 such as circle 601. Next, the user selects a destination cell, for example by selecting a cell 620 in destination arrangement 607. The user is then prompted to enter an amount of the selected component to be assigned to the selected destination cell. Alternatively, the user may specify the amount of the component to be assigned to the destination cell by defining an equation as will be described below.

The user may define a mapping from multiple sources (including multiple regions in one destination) to multiple regions in another destination (or, if desired to another set of regions in the same destination) by, for example, selecting "many-to-many" mapping button 614. The user selects a group of cells in the starting destination, for example by dragging a cursor over the desired cells in destination arrangement 607, and a group of cells in the target destination (which may or may not be the same as the starting destination). The group of target cells may include any number of cells in the destination, and may include one or more rows or columns of cells, or parts of one or more rows or columns. Design module 130 prompts the user to input an amount of a component or components to be assigned from the selected starting cells to the selected target cells through user interface 160.

Optionally, the user may define a one-to-one or many-to-many mapping by reference to an appropriate text file, such as, for example, a tab-delimited spreadsheet file generated by Microsoft® Excel, by selecting an appropriate button 616 or 617. Design module 130 prompts the user to identify a source or sources and destination region or regions, and prompts the user to select a file containing the desired mapping information. Design module 130 assigns the selected component or components to the cells of the selected destination according to the contents of the selected file. Thus, for example, the selected file may contain a tab-delimited array of constant values used to assign components to the corresponding cells of a selected destination array. Alternatively, design module 130 may calculate the amount of one or more components to be assigned to each cell in a selected destination based on equations, such as exponential, logarithmic, polynomial or geometric expressions or the like, contained in the selected file.

The user defines a mapping from a source to multiple destination cells by, for example, selecting a "one-to-many" mapping button 613. Design module 130 prompts the user to select a desired source and a group of cells in a desired destination, as described above. Design module 130 then prompts the user to specify a distribution scheme to be applied over the selected destination cells, for example defining a linear distribution gradient by entering starting and ending amounts, a direction and a distribution pattern (such as rectangular, triangular or other desired shape).

Figure 6A:
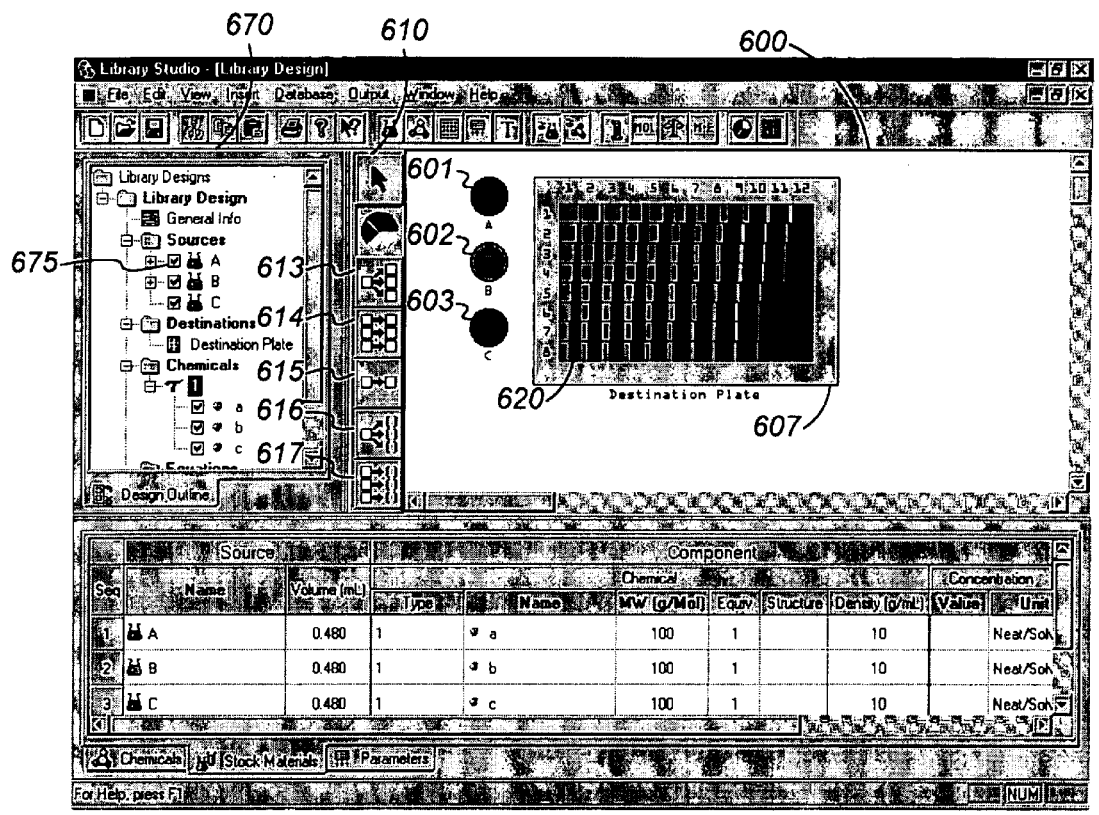
FIG. 6A is an illustrative library design window of the system user interface including a pane for graphically defining a library by mapping.
Figure 6B:
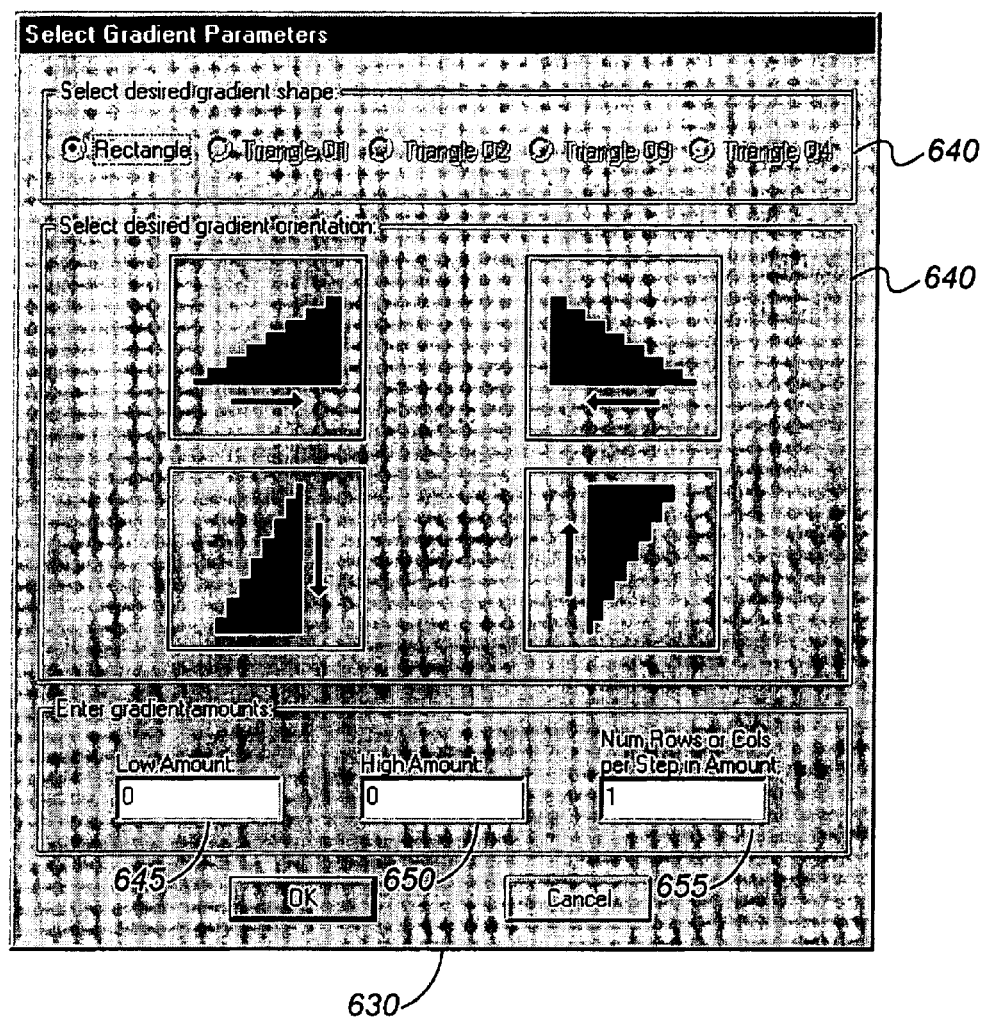
FIG. 6B is an example of a dialog for defining a gradient mapping object.

FIG. 6B shows one implementation of a dialog for defining a mapping distribution in more detail. Dialog 630 includes a pane 635 of radio buttons providing the user with a choice of various gradient shapes, such as rectangular or triangular. In pane 640, the user selects a gradient orientation—the direction or directions in the destination array along which the amount of the component increases. The user inputs the minimum and maximum values for the gradient in fields 645 and 650, and enters a number of rows or columns in the destination specifying the step size of the gradient in field 655. Design module 130 calculates an amount for each selected cell in the destination, beginning with the minimum amount in the first cell and increasing to the maximum amount according to the specified gradient.

In other embodiments, user interface 160 and design module 130 can be configured to define mappings based on other distribution schemes. For example, while the embodiment shown in FIG. 6B illustrates a dialog for defining a linear gradient, user interface 160 and design module 130 can be configured to define gradients according to one or more other well known mathematical forms, such as exponential, logarithmic, polynomial or geometric functions. Likewise, design module 130 can be configured to define "many-to-one" mappings for assigning amounts of material from multiple sources to a single destination region, using constant amounts of material from each source or varying amounts defined by gradients as described above. In still another embodiment, design module 130 can be configured to permit mapping from one source or sources to one or more others sources (or from a destination region or regions) to one or more sources.

While the embodiment shown in FIG. 6B provides for the definition of the gradient without reference to specific units of measure, user interface 160 and design module 130 can be configured to permit the user to input values in any convenient measure, such as, for example, units of molarity, weight, volume or thickness. In such embodiments, design module 130 automatically converts the selected units into appropriate units for calculation of mapping amounts, relieving the user of responsibility for making the necessary conversions. Thus, the user may define the sources for a library design using units that are most convenient for preparing stock solutions of components and design the library in another set of units more appropriate for that purpose, while design module 130 outputs a recipe file in still another set of units appropriate for synthesis of the library.

The user may view the properties of each defined mapping object (e.g., sources, destinations, amounts, shape, and the like) and the overall mapping sequence through an appropriate mapping dialog, such as dialog, 660 in FIG. 6C, accessed, for example, by selecting an appropriate menu item, toolbar button or other graphical device in user interface 160. The results of applying each defined mapping to a selected destination are displayed in graphical pane 600, which graphically depicts the composition of each destination region in the current library design. In the embodiment illustrated in FIG. 6A, composition data for destination arrangement. 607 is displayed in layered chart form, with each cell in the destination being divided into colored or patterned layers or bars the size of which represents the relative amount of each component assigned to that cell. By selecting or unselecting the check box associated with each source (or chemical, depending on the selected view option) in outline pane 670 in FIG. 6A, the user may view the relative proportion of some or all components assigned to a given cell. Thus, for example, if the user deselects source A check box 675, design module 130 removes the layer corresponding to that source from each cell in array 607, allowing the user to view the relative proportions of the remaining components without regard to the amount of that source assigned to each destination region. Optionally, the user can view composition data in the form of an set of pie charts, described in more detail in connection with FIG. 8C, below, with each individual pie chart being divided into colored wedges depicting the relative amount of a corresponding component assigned to that destination region. The user can also access numerical compositional data in spreadsheet form by selecting an appropriate menu item, toolbar button or similar graphical device in user interface 160.

User interface 160 and design module 130 are also configured to enable the user to define a distribution scheme using systems of one or more equations defining the amount of a component or components, or the ratio between two or more such components, to be assigned to one or more destination regions. The user can employ such a "design by equations" mapping scheme to define mappings for the entire combinatorial library, or to define one or more mappings of a multi-mapping library design in combination with the gradient mapping implementation discussed above.

Figure 7A:
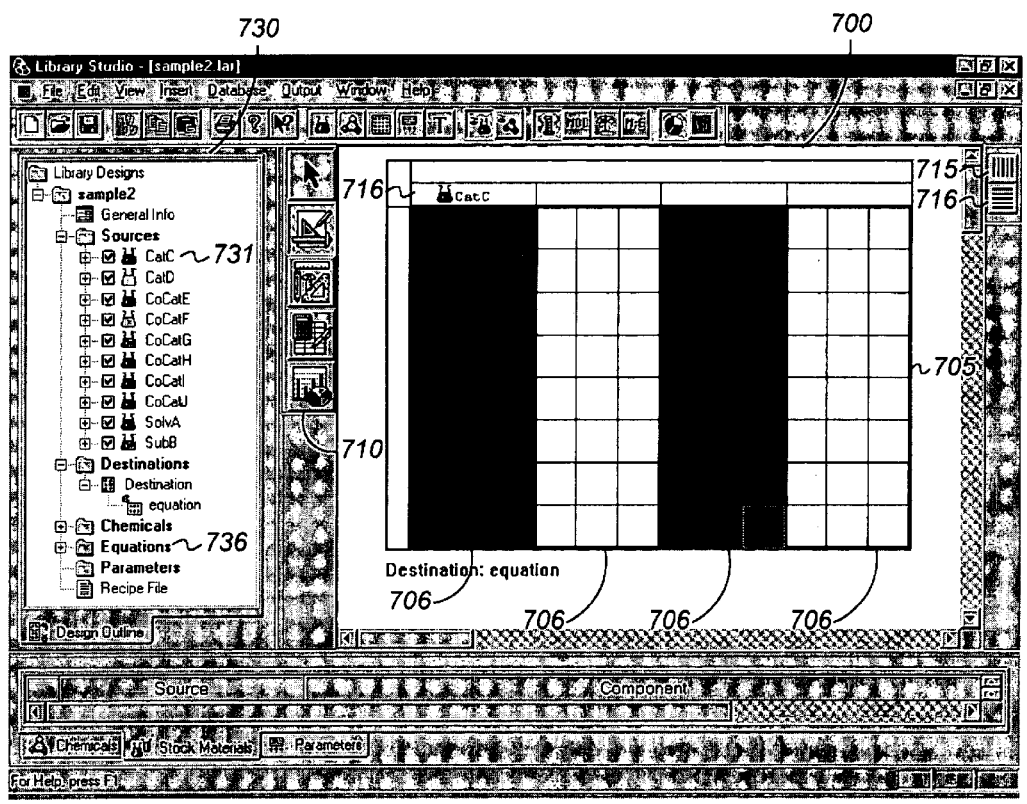
FIG. 7A is an illustrative library design window including a pane for defining a library using equations.

As shown in FIG. 7A, the user defines an equation by selecting an appropriate menu item or toolbar button, such as equation design button on toolbar 610, causing user interface 160 to display equation design arrangement 705 and associated equation design toolbar 710 in pane 700. The user initiates equation design by selecting Equation Design button 711, and partitions array 705 into regions, such as regions 706, 707, 708 and 709, for example by selecting the desired regions with a mouse or other input device. Selection of row partition or column partition buttons 715 and 716 causes design module 130 to insert a row or column header, such as column header 720, and creates a group of destination cells—for example, the group of cells in region 706—that will be governed by any equations assigned to the corresponding header. By repeating the partitioning operation with various sizes of destination regions, the user can create multiple row and column headers capable of applying multiple equations to the cells of destination arrangement 705 as will be described below.

The user may assign a component (i.e., a source or sources, including a chemical or chemicals) to a header by selecting the appropriate icon (e.g., icon 731) from the current library design folder in outline pane 730, and dragging the selected source and dropping it into the desired header 720 in destination arrangement 705. This action causes design module 130 to assign the component represented by source icon 731 to all cells assigned to header 720 for use in equations governing those cells as described below. Optionally, the user may assign components (sources or chemicals) to one or more individual cells or groups of cells by dragging the selected component and dropping it into the desired cell or cells.

The user may also assign multiple components to a destination by first defining an appropriate array of sources—for example an array of different chemicals of the same type—and dragging the source array onto the desired destination.

Figure 7B:
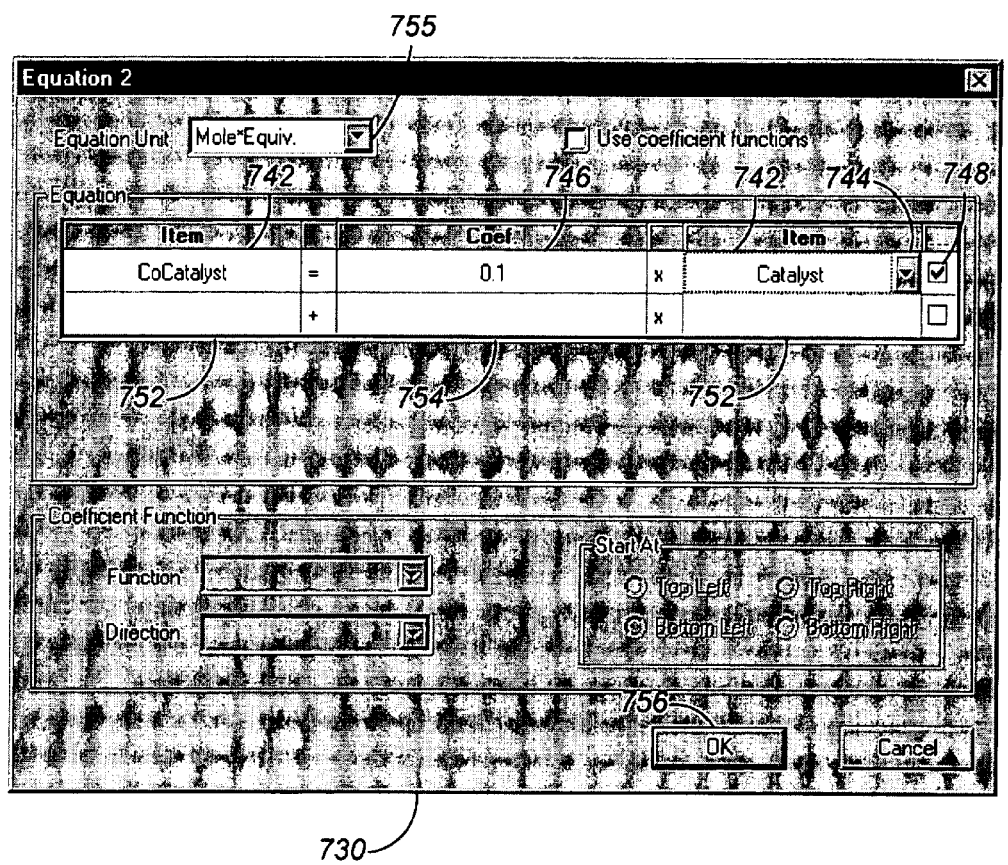
FIGS. 7B and 7C are illustrative dialogs for defining an equation object.

The user defines an equation by, for example, selecting a desired header and causing design module 130 to prompt the user to enter the relevant equation properties, for example through an equation property dialog 740 as shown in FIG. 7B. In dialog 740, the user defines a ratio equation describing a relationship between, for example, two or more components or chemical types as a sum of weighted terms. In fields 742, the user identifies the desired terms, which may include user-defined types or subtypes (e.g. catalysts, co-catalysts, solvents, initiators, monomers, surfactants, ligands, metals and the like), sources, chemicals or synthesis parameters such as total mass, total volume and the like. In one embodiment, terms in fields 742 may be selected from a list of available types, sources, chemicals and synthesis parameters by activating an arrow button 744 associated with a field 742 that invokes a pull-down menu identifying the available choices that have been defined as discussed above. The user enters coefficients defining the weighting of the selected term in coefficient fields 746. Additional types or subtypes, sources, chemicals or synthesis parameters can be incorporated in an equation by selecting box 748, which appends an additional line 750 to the equation, with additional term and coefficient fields 752 and 754. The user also selects an appropriate unit in unit field 755. Selection of OK button 756 causes design module 130 to assign the specified equation to the selected header. An icon representing the newly defined equation object is added to Equations folder 736 in outline pane 730.

Figure 7C:
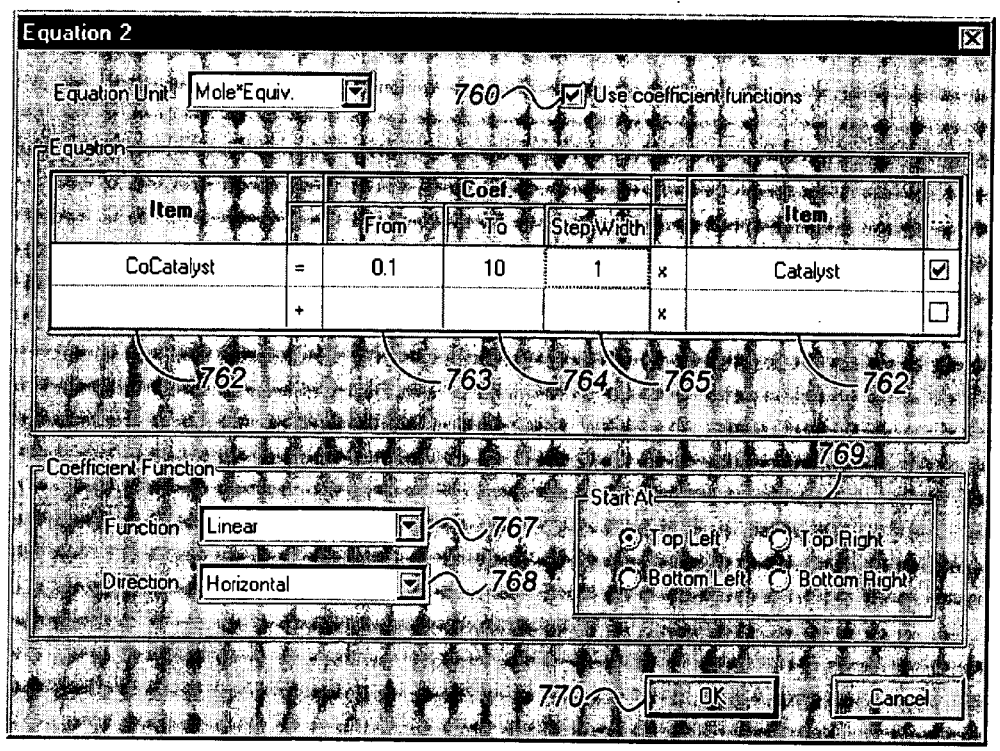

Referring to FIG. 7C, more complex relationships can be defined by using coefficient functions, accessed in this embodiment by selecting coefficient box 760. This feature permits the user to use equations to define gradients to be applied across the cells in a region governed by a particular equation. As described above, the user selects appropriate terms (types, sources, chemicals, synthesis parameters) in term fields 762, and enters minimum and maximum coefficient values in fields 763 and 764, entering a step value for the gradient in step width field 765. The user then selects a desired function defining the change in coefficient values, such as linear, exponential or logarithmic functions, in function field 767, and selects a gradient direction, such as horizontal, vertical or diagonal, in direction field 768. A starting point for application of the gradient is selected using radio buttons 769. Selection of OK button 770 causes design module 130 to assign the defined function to the selected header, and to add an icon representing the equation object to the Equations folder in outline pane 730.

The user may assign equations to individual destination cells or groups of cells. A pre-defined equation can be assigned to a cell or group of cells, for example by selecting the equation icon from Equations folder 736 in outline pane 730 and dragging the equation to a desired cell or group of cells, or by dragging the equation to a header governing a desired group of cells. The user may view a list of all equations defined for a particular cell, group of cells? or for the entire destination, for example in an equation list dialog window, and may copy equations from one cell or group of cells and assign those equations to another cell or group of cells, or to a header governing another group of cells.

Figures 8A, 8B:
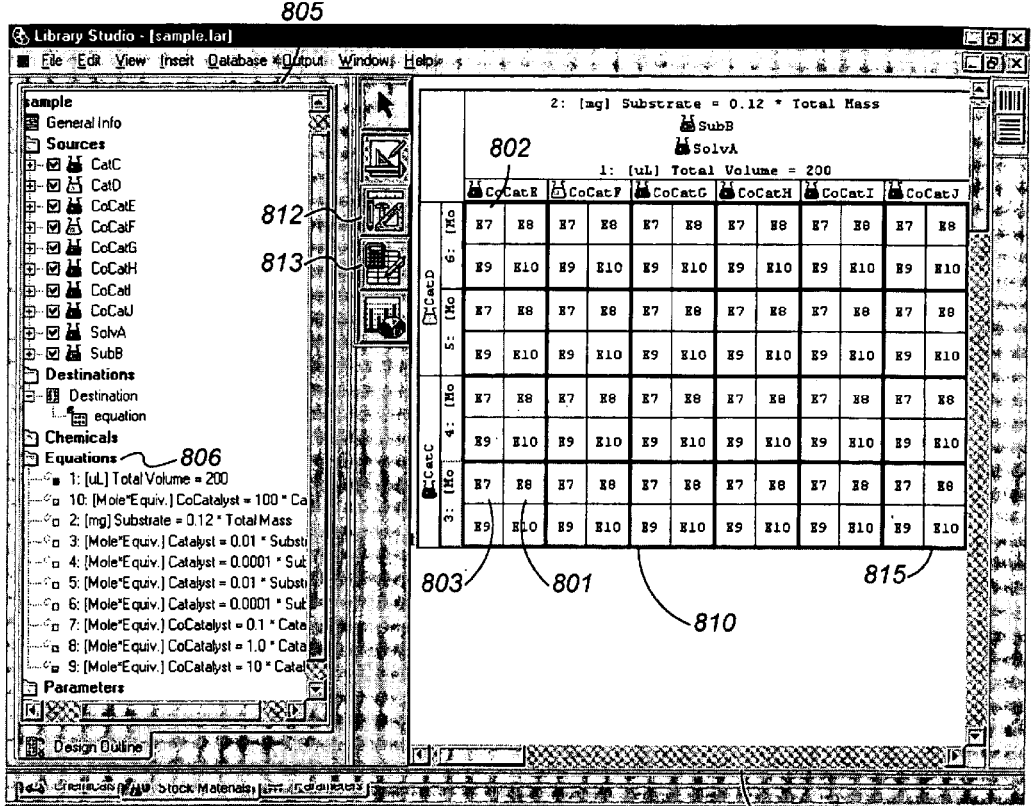
FIG. 8A is an illustrative library design window depicting an equation design.
FIG. 8B is an example of a dialog displaying the calculation of composition for a cell in an equation design.

FIG. 8A depicts a pane 800 illustrating a destination 810 for which a number of governing equations have been defined as described above. The user accesses this equation view of destination 800 by, for example, selecting an appropriate menu item or toolbar button, or by selecting arrangement 705 in FIG. 7A or array 607 in FIG. 6A with a mouse or other input device. Destination 810 includes rows and columns of cells 815 that correspond to the cells of arrangements 607 and/or 705. In this example, each cell 815 is depicted as including an equation designated as E7, E8, E9 or E10. The equations themselves are displayed as items in Equations folder 806 in outline pane 805.

Thus, for example, cells 801 to which equation E8 is assigned are subject to the equation

[Mole Equiv.]CoCatalyst=1.0*Catalyst, where CoCatalyst and Catalyst are chemical Types defined in the Chemicals layer of the corresponding definition pane. Each cell 801 is also governed by equations appearing in headers located above the column and to the left of the row in which that cell appears. The cell identified by reference numeral 802, for example, is subject to the following equations:

[Mole Equiv.]CoCatalyst=0.1*Catalyst

[uL]TotalVolume=200

[mg]Substrate=0.12*Total Mass

[Mole Equiv.]Catalyst=0.0001*Substrate while the cell identified by reference numeral 803 is subject to the following equations:

[Mole Equiv.]CoCatalyst=0.1*Catalyst

[uL]TotalVolume=200

[mg]Substrate=0.12*Total Mass

[Mole Equiv.]Catalyst=0.01*Substrate

As discussed above, the location of a given cell 801 also determines which specific components (chemicals or sources) are to be used to supply the Types specified by the relevant equations. Thus, for cell 802 discussed above, design module 130 will use Sources SolvA, SubB, CatD and CoCatE for Types Solvent, Substrate, Catalyst and CoCatalyst, respectively, in solving the set of equations that determine the composition of the corresponding region. That is, design module 130 will solve the following set of equations to calculate the composition of cell 802:

[Mole Equiv.]CoCatE=0.1*CatD

[uL]TotalVolume=200

[mg]SubB=0.12*Total Mass

[Mole Equiv.]CatD=0.0001*SubB

The use of subtypes provides the user additional flexibility in designing a library using equations. For example, a user may design a library for copolymerizing pairs of monomers, with the monomers being added at different times during the polymerization reaction. By defining two chemical subtypes—for example, "first monomer" and "second monomer"—under single chemical type "monomer", the user may define the total amount of combined monomer using one equation (e.g., [(mg) monomer=0.2 Total Mass]), while defining the ratio of the first monomer to the second monomer using a second equation (e.g., [(mg) first monomer=0.3 second monomer]).

In one embodiment, the user may cause design module 130 to verify that the set of defined equations is solvable at any time during the library design process, for example by selecting Check Mode button 812. In response to this selection, design module 130 performs a number of checks to determine whether the user has provided sufficient information to enable design module 130 to solve the set of equations. Thus, for example, design module 130 determines whether the user has provided all source information, such as chemical molecular weight, concentration, density and the like, that will be required by the set of equations. If design module 130 determines that all necessary source information has not been defined, design module 130 prompts the user to enter the necessary information through user interface 160. Design module 130 also determines whether the number of defamed equations matches the number of defined sources (and whether chemicals or sources of all appropriate Types have been assigned to each cell) and verifies that no equations are duplicated. For any cells that fail this equation check, design module 130 informs the user of an equation error through user interface 160, for example by displaying an appropriate error message or displaying the destination array with failed cells identified by an appropriate color or pattern, such as by displaying cells for which sufficient information has been defined in green and all other cells in red. Optionally, design module 130 also informs the user of the reason or reasons why the equations defined for a given cell cannot be solved.

Upon receiving user input indicating that equation design is complete (for example, by selection of Solve Equations button 813), design module 130 uses conventional matrix algebra techniques to solve the equations defined for a given destination to calculate the composition of the corresponding destination cells, substituting the appropriate Chemicals and Sources for Types included in the set of equations defined for each cell. Thus, for example, design module 130 uses techniques such as LU decomposition to solve a set of defined ratio equations, providing results in the form $X=X_1+X_2$, where $X_1$ is a sub-vector of chemical masses and $X_2$ is a sub-vector of volumes of stock materials. Design module 130 may be configured to accept and solve other types of equations, such as mass equations defined as:

$$[-I\ D]\begin{bmatrix}X_1\\X_2\end{bmatrix}=0,$$

where $X_1$ is a sub-vector of chemical masses and $X_2$ is a sub-vector of volumes of stock materials, I is the identity matrix and D is the density matrix.

The calculations with which design module 130 solves the set of equations for each cell may be internal to the computer and invisible to the user; optionally, design module 130 displays the calculations in a window through user interface 160. As described above in connection with Check Mode button 812, when solving equations design module 130 optionally identifies each cell for which the assigned equations have a valid solution with an appropriate color, pattern or other visual display scheme, while identifying cells for which the assigned equations are not solvable with another appropriate display scheme (such as, for example, display-ing cells with a valid solution in green and other cells in red). Design module 130 is configured to allow the user to "diagnose" the reason for the failure to solve a cell's equations by, for example, displaying in response to appropriate user input an Equation Matrix dialog 830, as shown in FIG. 8B. For a selected cell, here cell 802 in array 810, dialog 830 displays a status for the cell (e.g., "Equation solving failed"), as well as a spreadsheet 835 with regions corresponding to values derived from the equations assigned to the selected cell (840), values calculated from stock material concentrations defined in the definition pane (845) and equation solutions for chemical mass and stock solution volume (850). In the example depicted in FIG. 8B, solutions region 850 reveals that the calculated volume for SolvA is negative, rendering the equations assigned to cell 802 not solvable.

Figure 8C:
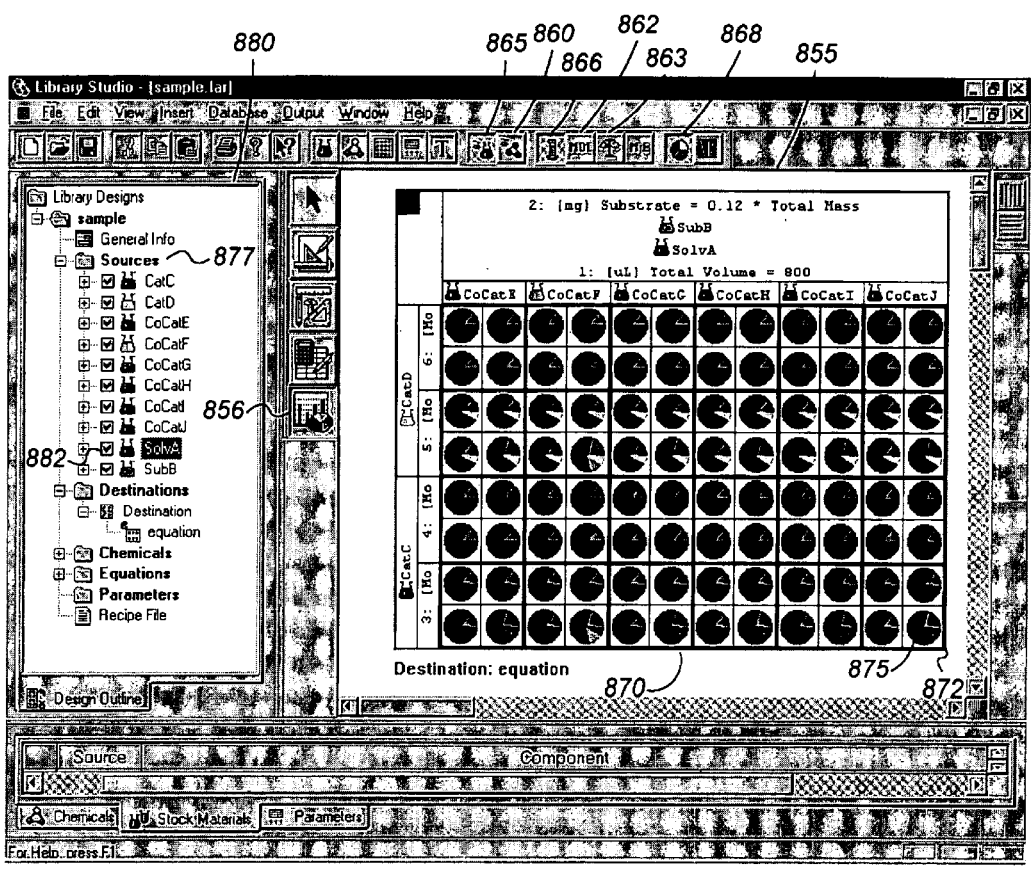
FIG. 8C is an illustrative library design window depicting the composition of a combinatorial library.

As shown in FIG. 8C, the user may view a graphic display of the calculated composition data resulting for an equation design by selecting an appropriate menu item of toolbar button, such as Display Data button 856 of graphical pane 855. The user may elect to view composition data by chemical mole or mass ratio, for example by selecting chemical button 860 and mole or mass buttons 862 or 863, respectively; alternatively, composition data may be displayed by source volume ratio by selecting source button 865 and corresponding volume button 866. Selection of pie chart button 868 causes design module 130 to display the composition data as an arrangement 870 of cells 872. Each cell 872 contains a pie chart 875 representing the calculated composition of the corresponding destination region determined by solution of the set of equations assigned to that cell. The relative proportion of each component assigned to the destination region (in units determined by the selected viewing option—volume for stock material solutions, mass or molarity for chemicals) is represented in each chart 875 by the size of a corresponding pie wedge depicted in a color or pattern associated with a given component (e.g., by colors assigned to each source component in Sources folder 877 in outline pane 880. By selecting or unselecting the check box associated with each source (or chemical, depending on the selected view option) in outline pane 880, the user may view the relative proportion of some or all components assigned to a given cell. Thus, for example, if the user deselects SolvA check box 882, design module 130 removes the pie wedge corresponding to that source from each pie chart 875 in arrangement 870, allowing the user to view the relative proportions of the remaining components without regard to the amount of solvent (SolvA) assigned to each destination region. The user may also view the calculated composition data in layered chart form as described above in connection with FIG. 6A, above. Numerical composition data for each destination region may be displayed through a cell composition data dialog 885, as shown in FIG. 8D.

Referring again to FIG. 3, in one embodiment, design module 130 is configured to enable the user to incorporate varying process parameters into a library design through parameters specifying a scheme of varying values across one or more destinations.

Figure 9A:
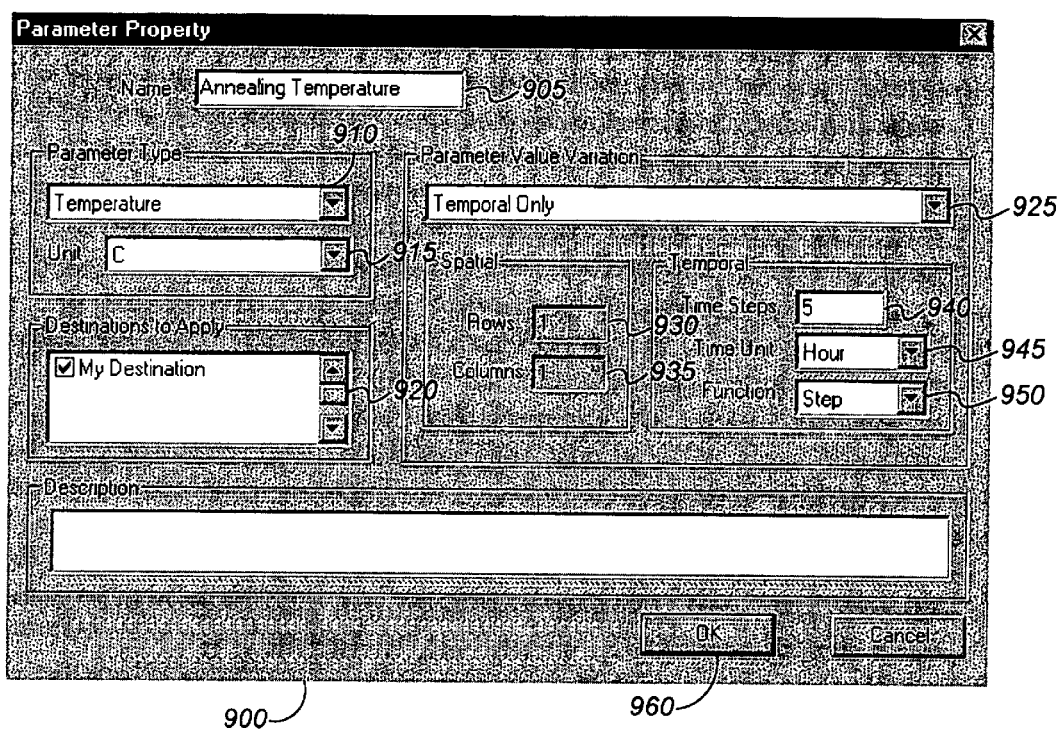
FIG. 9A is an example of a dialog for defining a process parameter object.

Parameters can include any external conditions, such as temperature, pressure, mixing speed, quench time, flow rate and the like. The user defines a parameter by, for example, selecting an appropriate menu item or toolbar button (step 330). Design module 130 prompts the user to enter the necessary information by displaying an appropriate dialog, such as Parameter Property dialog 900 shown in FIG. 9A. The user assigns a parameter name in name field 905 and selects a parameter type and appropriate units in fields 910 and 915. The user identifies one or more destinations in field 920 to which design module 130 will apply the defined parameter. In field 925, the user selects a scheme for varying the parameter values, which may include schemes such as temporal variation, spatial variation and the like, as well as combinations of such variation schemes. Design module 130 is configured to vary parameter values spatially, across one or more rows or columns, specified by the user in fields 930 and 935, respectively. Similarly, the user defines a temporal variation by specifying a time function (such as a linear function or a step function), a number of time steps and an appropriate time unit (such as seconds, minutes or hours) in fields 950, 940 and 945, respectively. The user may enter comments describing the parameter in comment field 955. Upon completion, signified, for example, by the user's selection of OK button 960, design module 130stores the parameter in memory 180, adds a corresponding parameter icon to parameter folder 515 in outline pane 510, and allocates space in the parameter layer of definition pane 530, as will be described next.

Figure 9B:
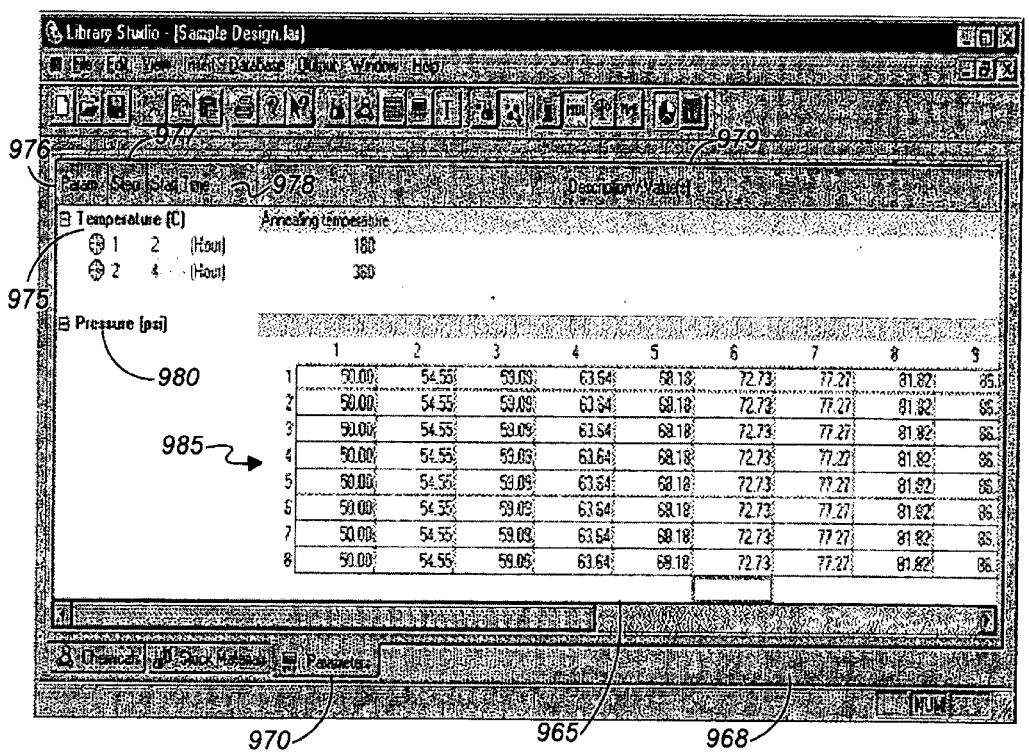
FIG. 9B is an example of a pane displaying the properties of parameter objects.

As shown in FIG. 9B, a parameter layer 965 is accessed by selecting parameter tab 970 in definition pane 968. Parameter layer 965 includes an entry for each defined parameter, such as Temperature parameter 975 and Pressure parameter 980. Each defined parameter is identified by an expandable entry identifying the parameter type (975, 980), which, upon expansion, displays the parameter properties input through Parameter Property dialog 900, as discussed above, such as a name 976, a step identifier 977, a start time 978 for each step, and a description or value for the parameter at that step 979. As appropriate, parameter layer 965 includes a spreadsheet-type display 985 depicting a parameter value for each cell in the destination to which the parameter is assigned in field 920 of Parameter Property dialog 900, as described above. Design module 130 is configured to allow the user to enter parameter values manually into parameter layer 965; alternatively, design module 130 populates parameter values according to a variation scheme defined in Parameter Property dialog 900, such as applying a constant or gradient function to a selected group of destination cells. The user can modify parameter values through Parameter Property dialog 900, or directly through parameter layer 965.

When library design is complete, the user may optionally store design files, including some or all of the design information—ie. the sources, destinations and parameters, as well as the mapping scheme and other related information—in memory 180. In one embodiment, design module 130 outputs a text file (or a tab-delimited spreadsheet file in a format suitable for a program such as Microsoft® Excel), describing the relative or absolute amounts of components to be deposited at each library member to allow a chemist to manually prepare the designed library. Alternatively, design module 130 can be configured to output an image file, such as Microsoft® PowerPoint file, depicting the graphical layer chart or pie chart display of composition data for a selected destination.

Design module 130 is also configured to generate a recipe file containing a set of synthesis instructions in a generic format that can be retrieved by synthesis module 140 for automated processing by material handling apparatus 180 (step 340 in FIG. 3). Appropriate apparatus 180 can include, for example, automated liquid handling robots, such as the RSP 900 Robotic Sample Processor, available from Cavro Scientific Instruments, Inc. of Sunnyvale, Calif. Apparatus 180 can also include automated systems performing different types of physical or chemical vapor deposition. In liquid handling, mixtures of solutions are typically dispensed in an array of miniature wells to create a library. In vacuum deposition, solid elements or chemicals or mixtures of solid elements or chemicals are vaporized and deposited as individual components on a substrate. The deposition may be controlled by a series of shutters and masks to manufacture the library. For an example of deposition equipment, see WO98/47613 (U.S. application Ser. No. 08/841,423), filed on Apr. 22, 1997.

In one embodiment, an appropriate data file or recipe file includes an entry for each source, each destination, each parameter, and each mapping created as described above, such as shown in Table 1 for the component labeled "CatA" in the equation design illustrated in FIG. 8A.

TABLE 1

[COMPONENT_1]

compLabel=CatA
libRegBegin=NULL
libRegEnd=NULL
arrayGeom=RECT
numRows=1
numColumns=1
[MAPPING_1]

Source=CatA
SourceRect=(1,1), (1,1)
Destination=Plate
DestRect=(2,2), (7,11)
GradientType=LIN
GradientParams=10.000000 0.0 0.0 −2.000000 0.000000 0.0 0.0 1 0
Tag=

Design module 130 graphically represents the recipe file for the current design as an icon 520 in outline pane 510 shown in FIG. 5A.

Figure 10:
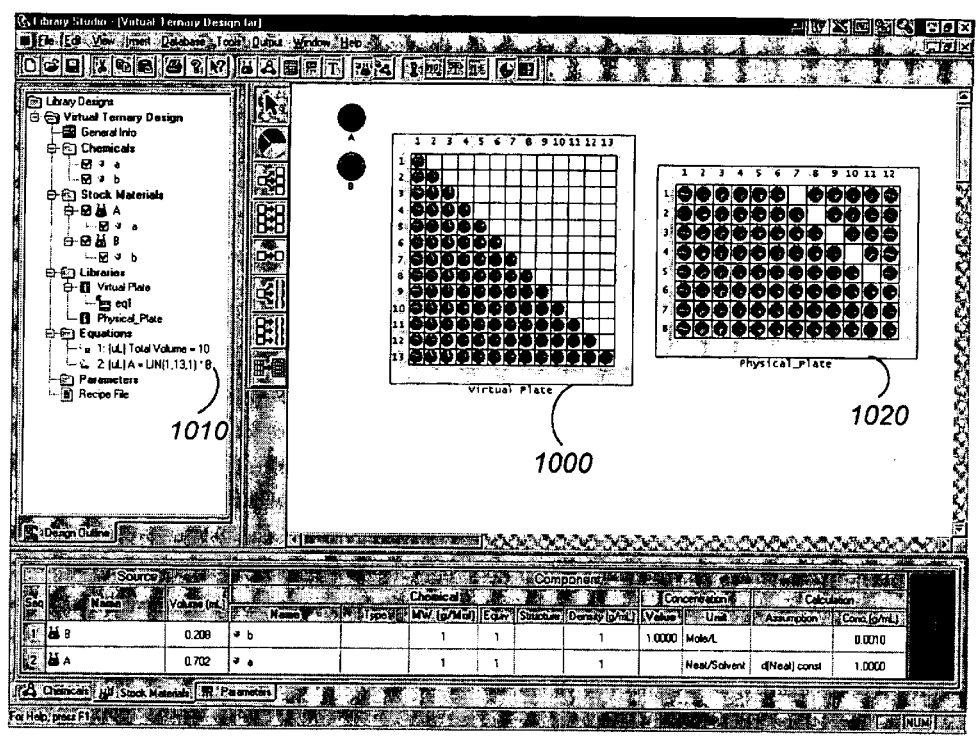
FIG. 10 is an example of a library design window depicting a virtual ternary library design mapped to a rectangular plate.

As described above, design module 130 creates a library design unconstrained by the physical limitations of available synthesis apparatus and library substrates. Thus, while the user may design a library using a destination arrangement containing the number of library members (i.e. individual reactors) in the same geometry (e.g., the number of rows and columns) as the physical substrate on which the library will ultimately be prepared, design module 130 enables the user to design libraries without regard to these constraints. Thus, the user may design a conceptual "virtual" library containing vast numbers of individual members (thus spanning multiple physical libraries), yet connected by a central chemical concept. Similarly, the user may also design a library in a preferred design environment (e.g., a geometry that best defines a library concept such as the ternary design shown in FIG. 4), while the design can be implemented in a different physical geometry for convenience of library synthesis. One such virtual library design is shown in FIG. 10. The user designs a library of varying compositions of sources A and B in ternary form on "Virtual Plate" destination 1000, with the amount of source A assigned to each cell determined by a linear gradient defined in equation 1010. Design module 130 then maps the 91 occupied cells of destination 1000 onto rectangular "Physical Plate" 1020 for implementation by conventional synthesis apparatus.

The user can also define a library design for use as a template in the design and preparation of multiple related libraries. Thus, for example, a library design of 96 different catalyst formulations may be used as a template to explore the polymerization of various organic monomers. Alternatively, a design can be defined for a portion of a single destination and used as a template to define multiple designs covering the entire destination—for example, the user may create a template design for a library of polymerization catalysts that covers only a single quadrant of an 8×12 destination and use the template to define a set of four library designs in which four different monomers are polymerized in the presence of the catalyst library. In this embodiment, the user designs the library as described above, with one source defined to correspond to one desired monomer, and stores the design in memory 150. The user may then retrieve the design and use design module 130 to create a series of library, one for each desired monomer, by simply replacing the defined monomer in the template design, recalculating the composition of each destination cell and generating the corresponding recipe file. More generally, the user may create a template design using a set of n design elements, where, for example, n defines the number sources used in the design, and instruct design module 130 and synthesis module 140 to generate a series of m libraries, where m>n and m is a number of actual sources used in preparing the libraries. Thus, while the library design may specify a combination of a limited number of design elements—for example, a quaternary library of inorganic materials in which each cell contains a mixture of four materials—the library design can be implemented for a larger number of elements, by creating a set of libraries encompassing all possible combinations/iterations of sources from the set of available sources—for example, by creating all possible combinations of four materials from a set of six available materials. Similar template designs can be created for designs involving any design elements—for example, multiple equation coefficients, multiple parameter values, or any combination of elements.

In one embodiment, design module 130 is configured to interact with a database 150 associated with system 100 that is capable of archiving information pertaining to available chemicals, stock materials, composition data for existing library designs and the like. In this embodiment, the user may search the database for chemicals based on relevant identifying information, such as chemical name, formula, identification number (e.g., CAS number) or the like. The user may select any chemicals identified in such a search, and design module 130 downloads chemical attribute information into the Chemicals layer in the current library design (e.g., definition pane 530 in FIG. 5A). To facilitate archiving and tracking of existing library designs, the user may register one or more libraries on a designed destination in a database 150 associated with system 100. Design module 130 assigns each library so registered an identification number with which each library may later be retrieved from database 150. Similarly, the user may load composition data for one or more libraries on a destination to database 150 for later retrieval.

The design methods and programs of the present invention can be advantageously applied in connection with the design and synthesis of libraries or arrays of diverse materials. Preferably, such diverse materials are candidate materials (e.g., catalysts) being evaluated for a desired chemical property, for example a capability to enhance a chemical process (e.g., chemical reaction) of interest.

A library of such materials can be a physical array of candidate materials, comprising a substrate and two or more different candidate materials, and preferably four or more different candidate materials at separate portions of the substrate, corresponding to library members. Each candidate material can consist essentially of two components (or source materials—e.g., a combination of sources A and B). Alternatively, additional components can be incorporated in the library design, resulting in libraries of diverse materials having compositions that are essentially ternary, quaternary or higher order. Such higher-order compositions can be designed to include the same components (e.g., A, B and C) in each composition, but in varying amounts or ratios, or alternatively, to include different components (e.g., A, B and C; A, B and D; A, B and E; A, B and F, etc.) in two or more of the compositions. In one preferred library, there is a spatially addressable array of materials that comprises a substrate having a surface and nine or more materials having different compositions at nine or more discrete regions of the substrate surface, with each material-containing region consisting essentially of one material. The nine or more materials preferably comprising two or more common components of interest, A and B, with the amount of at least one of the common components, A, preferably varying incrementally and uniformly between the nine or more materials, such that the nine or more materials form a uniform compositional gradient with respect to component A. The gradient can be linear, exponential, etc., as described above. The amount of one or more additional components (e.g., component B) can also vary. Non-gradient applications are also considered, as explained above in connection with the various mappings. In a particularly preferred library, the array comprises eleven or more materials at eleven or more discrete regions of the substrate, and at least one of the materials comprises component A and an essential absence of component B.

Appropriate candidate materials can include elements, compounds or compositions comprising a plurality of elements and/or compounds, and can be in a gaseous, liquid or solid phase. Solid-phase materials are preferred for some applications. The particular elements, compounds or compositions to be included in a library of candidate materials will depend upon the particulars of the chemical phenomenon or process being investigated. However, the nature of the particular chemical phenomenon or process being investigated is not critical, such processes can include, for example, chemical reactions and chemical separations, among others.

For example, candidate materials can include compositions that catalyze reactions including activation of, breaking and/or formation of H—Si, H—H, H—N, H—O, H—P, H—S, C—H, C—C, C=C, C≡C, C-halogen, C—N, —O, C—S, C—P, C—B and C—Si bonds among others. Exemplary chemical reactions for which reaction-enhancing materials may be identified according to the present invention include, without limitation, oxidation, reduction, hydrogenation, dehydrogenation (including transfer hydrogenation), hydration, dehydration, hydrosilylation, hydrocyanation, hydroformylation (including reductive hydroformylation), carbonylation, hydrocarbonylation, amidocarbonylation, hydrocarboxylation, hydroesterification, hydroamination, hetero-cross-coupling reaction, isomerization (including carbon-carbon double bond isomerization), dimerization, trimerization, polymerization, co-oligomerization (e.g. CO/alkene, CO/alkyne), co-polymerization (e.g. CO/alkene, CO/alkyne), insertion reaction, aziridation, metathesis (including olefin metathesis), carbon-hydrogen activation, cross coupling, Friedel-Crafts acylation and alkylation, Diels-Alder reactions, C—C coupling, Heck reactions, arylations, Fries rearrangement, vinylation, acetoxylation, aldol-type condensations, aminations, reductive aminations, epoxidations, hydrodechlorinations, hydrodesulfurations and Fischer-Tropsch reactions, asymmetric versions of any of the aforementioned reactions, and combinations of any of the aforementioned reactions in a complex reaction sequence of consecutive reactions. For chemical reactions, candidate materials can be generally classified as those materials which are chemically altered or consumed during the course of the reaction (e.g., co-reactant materials, cataloreactants) and those materials which are not chemically altered or consumed during the course of the reaction (e.g., catalysts, selective blocking moieties). In preferred applications, candidate materials are catalysts, which term, as used herein, is intended to include a material that enhances the reaction rate of a chemical reaction of interest or that allows a chemical reaction of interest to proceed where such reaction would not substantially proceed in the absence of the catalyst.

Appropriate candidate materials preferably include elements or compounds selected from the group consisting of inorganic materials, metal-ligand complexes and non-biological organic materials. In some applications, candidate materials will consist essentially of inorganic materials, consist essentially of metal-ligand materials, or consist essentially of non-biological organic materials. Moreover, in some applications, source and/or candidate materials will be compositions comprising mixtures of inorganic materials, metal-ligand materials, and/or non-biological organic materials in the various possible combinations.

Inorganic materials include elements (including carbon in its atomic or molecular forms), compounds that do not include covalent carbon-carbon bonds (but which could include carbon covalently bonded to other elements, e.g., $CO_2$), and compositions including elements and/or such compounds. Inorganic candidate materials that could be investigated in libraries designed according to the approaches described herein include, for example: noble metals such as Au, Ag, Pt, Ru, Rh, Pd, Ag, Os and Ir; transition metals such as Ti, V, Cr, Mn, Fe, Co, Ni, Cu, Zn, Y, Zr, Nb, Mo, Ta, W and Re; rare-earth metals such as La, Ce, Pr, Nd, Sm, Eu, Th, Th and U; alloys of noble metals, transition metals and/or rare-earth metals;

metal oxides such as CuO, NiO and $Co_3O_4$; noble-metal-doped metal oxides such as noble-metal-doped CuO, NiO and $Co_3O_4$; multi-metal oxides such as binary oxides of Cu—Cr, Cu—Mn, Cr—Mn, Ni—Cr, Ni—Mn, Ni—Cu, Ni—Mo, Cu—Mo, Ni—Co, Co—Mo, Ni—Fe, Fe—Mo, Cu—Fe, Mn—Ag, Mn—Sn, Ag—Sn, Cu—Ag, Cu—V, Ag—V, Cu—V, Ni—V, Bi—Mo, Bi—V, Mo—V, V—Zr, V—Ti, Zr—Ti, V—Nb, Nb—Mo, V—P, P—Mo, Ni—P, P—Cu, Co—P, Co—Fe, P—Fe, Mg—V, Mg—Sn, V—Sn, K—Ti, K—Bi, Ti—Bi, Cr—Sb, Cr—V, Sb—V, Bi—Mo, Bi—Nb, K—Cr, K—Al, Al—Cr, Zn—Cu, Zn—Al, Cu—Al, La—Cr, La—Zr, Cr—Zr, La—Mo, Mo—Zr, La—W, W—Zr, Mo—W, W—V, Cu—W, Bi—W, Fe—Sb, Fe—V and Ni—Ta, Ni—Nb and Ta—Nb, and such as ternary oxides of Cu—Cr—Mn, Ni—Cr—Mn, Ni—Cu—Mo, Ni—Co—Mo, Ni—Fe—Mo, Cu—Fe—Mo, Mn—Ag—Sn, Cu—Ag—V, Cu—Ni—V, Bi—Mo—V, V—Zr—Ti, V—Nb—Mo, V—P—Mo, Ni—P—Cu, Co—P—Fe,:Mg—V—Sn, K—Ti—Bi, Cr—Sb—V, Bi—Mo—Nb, K—Cr—Al, Zn—Cu—Al, La—Cr—Zr, La—Mo—Zr, La—W—Zr, Mo—W—V, Cu—Mo—W, Bi—Mo—W, Bi—V—W, Fe—21Y—; Sb—V and Ni—Ta—Nb; metal carbides such as PdC; metal sulfates, metal sulfides, metal chlorides, metal acetates, polyoxometallates (POM); metal phosphates such as vanadylpyrophosphates (VPO); Bronstead acids such as HF; Lewis Acids such as $AlCl_3$; and mixtures of any of the aforementioned inorganic materials, among others. Exemplary inorganic material libraries could include, for example, triangular-shaped arrays of ternary metal oxides (e.g. such as oxides of the ternary metal partners described above) with single metal oxide compounds at each corners, binary metal oxide compositions along each of the sides with varying ratios of constituents, and ternary metal oxide compositions in the interior regions of the triangular array with varying ratios of constituents. Libraries of inorganic candidate materials can be prepared, for example, according to the methods disclosed in U.S. Pat. No. 5,776,359 to Schultz et al.

Metal-ligand complexes comprise a central metal atom or ion surrounded by, associated with and/or bonded to other atoms, ions, molecules or compounds—collectively referred to as "ligands"—typically through a carbon (to form, e.g., an organometallic), nitrogen, phosphorous, sulfur or oxygen atom and/or one or more linker moieties. The one or more ligands typically bind to one or more metal center and/or remain associated therewith, and by such association, modify the shape, electronic and/or chemical properties of the active metal center(s) of the metal-ligand complex. The ligands can be organic (e.g., $^1$-aryl, alkenyl, alkynyl, cyclopentadienyl, CO, alkylidene, carbene) or inorganic (e.g., $Br^-$, $Cl^-$, $OH^-$, $NO^{2-}$, etc.), and can be charged or neutral. The ligand can be an ancilliary ligand, which remains associated with the metal center(s) as an integral constituent of the catalyst or compound, or can be a leaving group ligand, which may be replaced with an ancillary ligand or an activator component. Exemplary metals/metal ions include ions derived from, for example, simple salts (e.g., $AlCl_3$, $NiCl_2$, etc.), complex or mixed salts comprising both organic and inorganic ligands (e.g., $[(5C\text{-}_5Me_5)IrCl_2]_2$, etc.) and metal complexes (e.g., $Gd(NTA)_2$, CuEDTA, etc.), and can generally include, for example, main group metal ions, transition metal ions, lanthanide ions, etc.

Libraries of metal-ligand candidate materials designed according to the methods and programs described herein can be prepared, for example, according to the methods disclosed in PCT Patent Application WO 98/03521 of Weinberg et al. Briefly, a desired ligand can be combined with a metal atom, ion, compound or other metal precursor compound. In many applications, the ligands will be combined with such a metal compound or precursor and the product of such combination is not determined, if a product forms. For example, the ligand may be added to a reaction vessel at the same time as the metal or metal precursor compound along with the reactants. The metal precursor compounds may be characterized by the general formula $M(L)_n$ (also referred to as $ML_n$ or $M\text{-}L_n$) where M is a metal and can include metals selected from the group consisting of Groups 5, 6, 7, 8, 9 and 10 of the Periodic Table of Elements. In some embodiments, M can be selected from the group consisting of Ni, Pd, Fe, Pt, Ru, Rh, Co and Ir. L is a ligand and can be selected from the group consisting of halide, alkyl, substituted alkyl, cycloalkyl, substituted cycloalkyl, heterocycloalkyl, substituted heterocycloalkyl, aryl, substituted aryl, heteroaryl, substituted heteroaryl, alkoxy, aryloxy, hydroxy, boryl, silyl, hydrido, thio, seleno, phosphino, amino, and combinations thereof, among others. When L is a charged ligand, L can be selected from the group consisting of hydrogen, halogens, alkyl, substituted alkyl, cycloalkyl, substituted cycloalkyl, heteroalkyl, heterocycloalkyl, substituted heterocycloalkyl, aryl, substituted aryl, heteroaryl, substituted heteroaryl, alkoxy, aryloxy, silyl, boryl, phosphino, amino, thio, seleno, and combinations thereof. When L is a neutral ligand, L can be selected from the group consisting of carbon monoxide, isocyanide, nitrous oxide, $PA_3$, $NA_3$, $OA_2$, $SA_2$, $SeA_2$, and combinations thereof, wherein each A is independently selected from a group consisting of alkyl, substituted alkyl, heteroalkyl, cycloalkyl, substituted cycloalkyl, heterocycloalkyl, substituted heterocycloalkyl, aryl, substituted aryl, heteroaryl, substituted heteroaryl, alkoxy, aryloxy, silyl, and amino. Specific examples of suitable metal precursor compounds include $Pd(dba)_2$ (dba= dibenzylydieneacteone), $Pd_2(dba)_3$, $Pd(OAc)_2$ (Ac=acetate), $PdCl_2$, $Pd(TFA)_2$, (TFA=trifluoroacetate), $(CH_3CN)_2PdCl_2$, and the like. In this context, the ligand to metal precursor compound ratio is in the range of about 0.01:1 to about 100:1, more preferably in the range of about 0.5:1 to about 20:1. The metal atom, ion or metal precursor may be supported or not. Supports may be organic or inorganic. Similar to the ligands, the support may be an L. In other embodiments, the support will not form part of the metal precursor and suitable supports include silicas, aluminas, zeolites, polyethyleneglycols, polystyrenes, polyesters, polyamides, peptides and the like. Specific examples of Pd supported metals include Pd/C, $Pd/SiO_2$, $Pd/CaCO_3$, $Pd/BaCO_3$, Pd/aluminate, Pd/aluminum oxide, Pd/polystyrene, although any of the metals listed above could replace Pd in this list, e.g., Ni/C, etc. In other applications, the ligand will be mixed with a suitable metal precursor compound prior to or simultaneous with allowing the mixture to be contacted to the reactants. When the ligand is mixed with the metal precursor compound, a metal-ligand complex may be formed, which may be employed as a candidate material.

Non-biological organic materials include organic materials other than biological materials. Organic materials are considered to include compounds having covalent carbon-carbon bonds. Biological materials are considered to include nucleic acid polymers (e.g., DNA, RNA) amino acid polymers (e.g., enzymes) and small organic compounds (e.g., steroids, hormones) where the small organic compounds have biological activity, especially biological activity for humans or commercially significant animals such as pets and livestock, and where the small organic compounds are used primarily for therapeutic or diagnostic purposes. While biological materials are of immense commercial interest with respect to pharmaceutical and biotechnological applications, a large number of commercially significant applications involve chemical processes that are enhanced by other than biological materials. Moreover, while fundamental screening approaches for many pharmaceutical and biological activities are known or readily adapted from known approaches, screening approaches for non-biological materials have not heretofore been widely investigated and reported. Although candidate materials being screened are preferably not, themselves, biological organic materials, candidate materials included in libraries designed according to the invention (e.g., inorganic materials) can be employed to enhance reactions directed to producing a biological organic material as the product of a chemical reaction (e.g., materials that enhance chemical-based, non-enyzmatic DNA synthesis, or materials that enhance a synthetic, non-enyzrnatic route to a particular hormone or steroid).

The amount of an individual candidate material located in a particular library member varies depending upon the required application and the method by which the library is prepared. For thin films, for example, the amount of material will depend on the surface area of the film and the required thickness of the film, each of which will, in turn, vary depending upon the chemical process of interest. For catalyst applications, the geometry of the reactor, and the required residence time or contact time of reactants in the reactor, among other factors, will also be important. In general, the amount of an individual candidate material is typically not more than about 25 mg, preferably not more than about 10 mg, and can be not more than about 7 mg, not more than about 5 mg, not more than about 3 mg and not more than about 1 mg. In preferred embodiments, the amount of an individual candidate material can range from about 0.1 g to about 100 mg, preferably from about 1 g to about 10 mg, more preferably from about 10 g to about 10 mg and most preferably from about 100 g to about 1 mg.

Libraries designed according to the methods discussed above can be prepared on any convenient substrate, including any suitable material having a rigid or semi-rigid surface on which the candidate materials can be formed or deposited or to which the candidate materials can be linked. The substrate preferably consists essentially of materials that are inert with respect to the materials and chemical processes of interest. Certain materials will, therefore, be less desirably employed as a substrate material for certain reaction process conditions (e.g., high temperatures—especially temperatures greater than about 100° C.—or high pressures) and/or for certain reaction mechanisms. The substrate material is also preferably selected for suitability in connection with microfabrication techniques, such as selective etching (e.g., chemical etching in a liquid or gaseous phase, plasma-assisted etching, and other etching techniques) photolithography, and other techniques known or later-developed in the art. Silicon, including polycrystalline silicon, single-crystal silicon, sputtered silicon, and silica ($SiO_2$) in any of its forms (quartz, glass, etc.) are preferred substrate materials. Other known materials (e.g., silicon nitride, silicon carbide, metal oxides (e.g., alumina), mixed metal oxides, metal halides (e.g., magnesium chloride), minerals, zeolites, and ceramics) may also be suitable for a substrate material. Organic and inorganic polymers may also be suitably employed in some applications of the invention.

Appropriate substrates may, but need not necessarily, have at least one substantially flat, substantially planar surface, and may preferably, but not necessarily, be a substantially planar substrate such as a wafer. The surface of the substrate can be divided into physically separate regions and can have, for example, dimples, wells, raised regions, etched trenches, or the like formed in the surface. In still other embodiments, small beads or pellets may be the substrate, and such beads or pellets may be included in an array, for example, for example, placing the beads within dimples, wells or within or upon other regions of the substrate's surface. Frits can be used to hold such beads or pellets in place. In other applications, the substrate can be a porous material. The substrate can, and is preferably, passive—having an essential absence of any active microcomponents such as valves, pumps, active heating elements, active mixing elements. The substrate also preferably has an essential absence of passive microcomponents such as microfluidic channels or apertures used for fluid distribution, heat-transfer elements, mass-transfer elements (e.g., membranes), etc., or combinations thereof. In some applications, however, the substrate can include such active microcomponents or such passive microcomponents. In a preferred application, the substrate has a substantially flat upper surface with a plurality of substantially coplanar indentations or wells of sufficient depth to allow a quantity of candidate material to be deposited, formed or contained therein. The overall size and/or shape of the substrate is not limiting to the invention. The size can be chosen, however, to be compatible with commercial availability, existing fabrication techniques (e.g., silicon wafer availability and/or fabrication), and/or analytical measurement techniques. Generally, the substrate will be sized to be portable by humans and/or to be manipulated by automated substrate-handling devices. Hence, two inch and three inch wafers are suitably employed. The choice of an appropriate substrate material and/or form for certain applications will be apparent to those of skill in the art based on the guidance provided herein.

In libraries prepared from library designs generated according to the methods discussed above, the candidate materials are generally deposited in a plurality of library members arranged on a substrate. The desired configuration of the candidate material with respect to the substrate depends upon the application. Thus, for example, for a library of candidate catalyst materials, the library can be configured in any design that allows for one or more reactants to contact the candidate material during the chemical reaction or other chemical process. Hence, it can be appreciated that the exact configuration of the candidate materials and the substrate are not limiting to the invention. Typical configurations generally allow for fluid flow past and around a candidate material formed on a surface of a reaction cavity, for unidirectional flow of reactants through a porous substrate or through a bed of beads, or for flow of reactants into and out of a well comprising a porous or non-porous substrate.

The candidate materials are preferably spatially separated in the library of candidate materials, preferably at an exposed surface of the substrate, such that the array of materials can, for example, be integrated with a plurality of microreactors to include different candidate materials within different microreactors for screening individual candidate materials for chemical properties of interest. Moreover, individual library members are also preferably separately addressable, for example, for analytical characterization thereof. The two or more different candidate materials are therefore preferably located at discrete, non-contiguous, individually addressable regions of the substrate, with the regions being spaced to accommodate inclusion into a plurality of microreactors. The different candidate materials may, nonetheless, also be contiguous with each other (e.g. as in a continuous gradient of different material compositions). However, even where a spatially separated, individually addressable array of candidate materials is desired in the ultimate physical library, the library design need not have these features, which may be incorporated by appropriate synthesis apparatus or by software controlling such apparatus.

If the two or more candidate materials are to be deposited on distinct, individually addressable regions of the substrate, the separation between adjacent regions can range from about to about 50 m to about 1 cm, more preferably from about 100 m to about 7 mm, and most preferably from about 1 mm to about 5 mm. The inter-region spacings can be not more than about 1 cm, not more than about 7 mm, not more than about 5 mm, not more than about 4 mm, not more than about 2 mm, not more 1 mm, not more than about 100 m, and not more than about 50 m. Exemplary inter-regions spacings (center-to-center) based on preferred embodiments of the invention are 4 mm for having 256 addressable regions on a three-inch wafer substrate, and 2 mm for having 1024 addressable regions on a three-inch wafer substrate. As such, the surface density of discrete candidate material regions can range from about 1 region/$cm^2$ to about 200 regions/$cm^2$, more preferably from about 5 regions/$cm^2$ to about 100 regions/$cm^2$, and most preferably from about 10 regions/$cm^2$ to about 50 regions/$cm^2$. The planar density can be at least 1 region/$cm^2$, at least 5 regions/$cm^2$, at least 10 regions/$cm^2$, at least 25 regions/$cm^2$, at 50 regions/$cm^2$, at least 100 regions/$cm^2$, and at least 200 regions/$cm^2$. For some reactions, lower or mid-range densities may be preferred. For other reactions, higher densities-may be suitable. Additionally, even higher densities may be achieved as fabrication technology develops to nano-scale applications.

The number of candidate materials to be included on a physical library is not narrowly critical, and can range, for example, from two to about a million or more, ultimately depending on available fabrication techniques and the nature of the chemical phenomenon or process being investigated. More specifically, the number of different candidate materials incorporated in a library is at least 2, preferably at least 5, more preferably at least 10, still more preferably at least 25, even more preferably at least 50, yet more preferably at least 100, and most preferably at least 250. Present microscale and nanoscale fabrication techniques can be used, however, to prepare arrays having an even greater number of different candidate materials. For higher throughput operations, for example, the number of different candidate materials can be at least about 1000, more preferably at least about 10,000, even more preferably at least about 100,000, and most preferably at least about 1,000,000 or more. The fabrication of arrays comprising very large numbers of different candidate materials is enabled by fabrication techniques known in the integrated circuit arts. See, for example, S. M. Sze, *Semiconductor Sensors*, Chap. 2, pp. 17–96, John Wiley & Sons, Inc. (1994). Such approaches have been adapted in other aspects of catalyst research. See, for example, Johansson et al., *Nanofabrication of Model Catalysts and Simulations of their Reaction Kinetics*, J. Vac. Sci. Technol., 17:1 (January/February 1999).

The invention can be implemented in digital electronic circuitry, or in computer hardware, firmware, software, or in combinations of them. Apparatus of the invention can be implemented in a computer program product tangibly embodied in a machine-readable storage device for execution by a programmable processor; and method steps of the invention can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in assembly or machine language if desired, or in a high-level procedural or object-oriented programming language, in which case individual design elements can be embodied as data objects in classes having sets of associated properties; in any case, the language can be a compiled or interpreted language. Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits).

To provide for interaction with a user, the invention can be implemented on a computer system having a display device such as a monitor or LCD screen for displaying information to the user and a keyboard and a pointing device such as a mouse or a trackball by which the user can provide input to the computer system. The computer system can be programmed to provide a graphical user interface through which computer programs interact with users.

The invention has been described in terms of particular embodiments. Other embodiments are within the scope of the following claims. For example, the steps of the invention can be performed in a different order and still achieve desirable results.

What is claimed is:

1. A computer-implemented method for generating a library design for a combinatorial library of materials, comprising:
   defining one or more sources and one or more destinations, each source being electronic data representing a component to be used in preparing the combinatorial library and each destination being electronic data representing an arrangement of cells;
   receiving an input defining a first mapping, the first mapping being electronic data defining a distribution pattern for assigning a component to cells in the arrangement, the distribution pattern including a minimum and a maximum amount of the component to be assigned to any cell of the arrangement and a gradient to be applied between the minimum and maximum amounts of the component across the plurality of cells;
   using the first mapping to calculate a composition of one or more materials assigned to one or more of the cells; and
   generating a representation of the library design, the representation comprising electronic data representing the sources, the destinations and the mapping.

2. The method of claim 1, further comprising:
   displaying a visual representation of the library design, the visual representation graphically describing the composition of one or more materials assigned to one or more of the cells.

3. The method of claim 1, wherein the representation comprises electronic data representing one or more sets of properties, each set of properties being associated with one of the sources, the destinations or the mapping.

4. The method of claim 1, wherein defining the sources and destinations comprises receiving an input from a graphical input device.

5. The method of claim 1, wherein the input defining a first mapping comprises a selection from a set of available mapping types, the set of available mapping types comprising a one to one mapping of a component from a source to a cell in the arrangement and a one to many mapping of a component from a source to a plurality of cells in the arrangement.

6. The method of claim 5, wherein the set of available mapping types further comprises a many to many mapping of a plurality of components from a plurality of sources to a plurality of cells in the arrangement.

7. The method of claim 6, wherein the set of available mapping types further comprises a many to one mapping of a plurality of components from a plurality of sources to a cell in the arrangement.

8. The method of claim 5, wherein the set of available mapping types further comprises a set of one or more user-defined equations.

9. The method of claim 1, wherein the gradient is selected from the group consisting of linear, logarithmic, exponential, polynomial and geometric progression.

10. The method of claim 3, wherein the set of properties associated with the mapping comprises a source name, a source geometry, a destination name, a destination geometry, a gradient type, and a set of gradient parameters defining the gradient.

11. The method of claim 1, further comprising:
    receiving an input defining a second mapping, the second mapping being electronic data defining a second distribution pattern for distributing a second component to cells in the arrangement; and
    using the first and second mappings to calculate a composition of one or more materials assigned to one or more of the cells.

12. The method of claim 11, wherein the second distribution pattern for assigning a second component includes electronic data identifying a fixed amount of the second component to be assigned to one or more cells in the arrangement.

13. The method of claim 12, wherein the second distribution pattern for assigning a second component includes electronic data identifying a minimum and a maximum amount of the second component to be assigned to any of the cells of the arrangement and a second gradient to be applied between the minimum and maximum amounts of the second component across the cells.

14. The method of claim 1, further comprising generating a modified library design by:
    receiving an input redefining a source, a destination or a mapping;
    recalculating the composition of one or more materials assigned to one or more of the cells; and
    generating a representation of the modified library design.

15. The method of claim 1, further comprising:
    receiving an input defining one or more parameters, each parameter being electronic data corresponding to a process parameter to be applied to one or more cells of the arrangement and defining a parameter value for the one or more cells of the arrangement, the parameter value varying between a minimum and a maximum amount; and
    wherein the representation further comprises electronic data representing the one or more parameters.

16. The method of claim 1, wherein the arrangement comprises two or more cells.

17. The method of claim 1, wherein the arrangement comprises ten or more cells.

18. The method of claim 1, wherein the arrangement comprises about ninety-six or more cells.

19. A computer-implemented method for generating a library design for a combinatorial library of materials, comprising:
    defining a set of one or more sources and one or more destinations, each source being electronic data representing a component to be used in preparing the combinatorial library and each destination being electronic data representing an arrangement of cells;
    receiving an input defining a set of first mappings, the first mappings being electronic data defining a set of equations for calculating an amount of one or more components to be assigned to one or more cells in an arrangement;
    using the set of equations to calculate a composition of a material assigned to one or more of the cells; and generating a representation of the library design, the representation comprising electronic data representing the sources, the destinations and the mappings.

20. The method of claim 19, further comprising:
displaying a visual representation of the library design, the visual representation graphically describing the composition of one or more materials assigned to one or more of the cells.

21. The method of claim 19, wherein the component to be assigned to a cell in the arrangement is determined by the location of the cell within the arrangement.

22. The method of claim 21, wherein the composition of a material is determined using a subset of the set of equations, the subset of equations being determined by the location of the cell within the arrangement.

23. The method of claim 19, further comprising:
generating an error indicator signal if the number of equations in the set of equations is not equal to the number of sources in the set of sources.

24. The method of claim 19, wherein at least one of the set of equations is selected from the group consisting of:
a ratio equation defining an amount of a component to be assigned to a cell as a function of an amount of another component to be assigned to the cell;
a volume equation defining an amount of a component to be assigned to a cell as a function of a total volume of a plurality of components to be assigned to the cell; and
a mass equation defining an amount of a component to be assigned to a cell as a function of a total mass of a plurality of components to be assigned to the cell.

25. The method of claim 19, wherein the set of equations comprises a gradient equation defining an amount of a component to be assigned to each of a plurality of cells according to a gradient.

26. The method of claim 19, wherein each of the set of equations is assigned to one or more cells of the arrangement according to the location of the cells within the arrangement.

27. The method of claim 19, wherein using the set of equations to calculate a composition of a material assigned to one or more of the cells comprises simultaneously solving a set of interdependent equations.

28. The method of claim 27, wherein using the set of equations further comprises using a matrix inversion technique to solve the set of equations.

29. The method of claim 19, further comprising:
receiving an input defining a second mapping, the second mapping being electronic data defining a distribution pattern for distributing a component to cells in the arrangement, the distribution pattern including a minimum and a maximum amount of the component to be assigned to any cell of the cells of the arrangement and a gradient to be applied between the minimum and maximum amounts of the component across the plurality of cells; and
using the first set of mappings and the second mapping to calculate a composition of a material assigned to one or more of the cells.

30. A computer-implemented method for generating a library design for a combinatorial library of materials, comprising:
defining a set of one or more sources and one or more destinations, each source being electronic data representing a component to be used in preparing the combinatorial library and each destination being electronic data representing an arrangement of cells;
defining a plurality of mappings, the mappings in the aggregate defining a composition for each of a plurality of materials assigned to a plurality of cells in the arrangement;
receiving an input defining one or more parameters, each parameter being electronic data corresponding to a process parameter to be applied to one or more cells of the arrangement and defining a parameter value for the one or more cells of the arrangement, the parameter value varying between a minimum and a maximum amount; and
generating a representation of the library design, the representation comprising electronic data describing the source elements, the destination elements, the mappings and the parameters.

31. The method of claim 30, wherein the parameter value is defined to vary over time.

32. The method of claim 30, wherein the parameter value is defined to vary across two or more cells in the arrangement.

33. The method of claim 30, wherein the parameter value is defined to vary over time and across two or more cells in the arrangement.

34. The method of claim 30, wherein the parameter value varies according to a gradient selected from the group consisting of linear, logarithmic, exponential, polynomial and geometric progression.

35. The method of claim 30, wherein the parameter value corresponds to a process parameter selected from the group consisting of temperature, pressure, time, flow rate and stirring speed.

36. A computer-implemented method for preparing a combinatorial library of materials on a substrate, the method comprising:
creating a library design by defining a set of design elements, the set of design elements including one or more sources representing components to be used in preparing the combinatorial library, one or more destinations, each destination comprising an arrangement of one or more cells, and one or more elements selected from the group consisting of a mapping defining a scheme for assigning one or more amounts of a component to one or more cells of an arrangement and a parameter corresponding to a process parameter to be applied to one or more cells of the arrangement, the parameter defining a parameter value for the one or more cells of the arrangement, the parameter value varying between a minimum and a maximum amount;
generating a representation of a library design, the representation comprising electronic data describing the sources, the destinations, the mappings and the parameters; and
using the representation to cause an automated material handling apparatus to assemble the combinatorial library on a substrate.

37. A computer program product on a computer-readable medium for generating a library design for a combinatorial library of materials, the computer program product comprising instructions operable to cause a programmable processor to:
receive an input defining one or more sources and one or more destinations, each source being electronic data representing a component to be used in preparing the combinatorial library and each destination being electronic data representing an arrangement of cells;
receive an input defining a first mapping, the first mapping being electronic data defining a distribution pattern for assigning a component to cells in the arrangement, the distribution pattern including a minimum and a maximum amount of the component to be assigned to any cell of the arrangement and a gradient to be applied between the minimum and maximum amounts of the component across the plurality of cells;

use the first mapping to calculate a composition of one or materials assigned to one or more of the cells; and generate a representation of the library design, the representation comprising electronic data representing the sources, the destinations and the mapping.

38. The computer program product of claim 37, further comprising instructions operable to cause a programmable processor to:

display a visual representation of the library design, the visual representation graphically describing the composition of one or more materials assigned to one or more of the cells.

39. The computer program product of claim 37, wherein the representation comprises electronic data representing one or more sets of properties, each set of properties being associated with one of the sources, the destinations or the mapping.

40. The computer program product of claim 37, wherein the input defining the sources and destinations comprises an input from a graphical input device.

41. The computer program product of claim 37, wherein the input defining a first mapping comprises a selection from a set of available mapping types, the set of available mapping types comprising a one to one mapping of a component from a source to a cell in the arrangement and a one to many mapping of a component from a source to a plurality of cells in the arrangement.

42. The computer program product of claim 41, wherein the set of available mapping types further comprises a many to many mapping of a plurality of components from a plurality of sources to a plurality of cells in the arrangement.

43. The computer program product of claim 42, wherein the set of available mapping types further comprises a many to one mapping of a plurality of components from a plurality of sources to a cell in the arrangement.

44. The computer program product of claim 40, wherein the set of available mapping types further comprises a set of one or more user-defined equations.

45. The computer program product of claim 37, wherein the gradient is selected from the group consisting of linear, logarithmic, exponential, polynomial and geometric progression.

46. The computer program product of claim 39, wherein the set of properties associated with the mapping comprises a source name, a source geometry, a destination name, a destination geometry, a gradient type, and a set of gradient parameters defining the gradient.

47. The computer program product of claim 37, further comprising instructions operable to cause a programmable processor to:

receive an input defining a second mapping, the second mapping being electronic data defining a second distribution pattern for distributing a second component to cells in the arrangement; and use the first and second mappings to calculate a composition of one or more materials assigned to one or more of the cells.

48. The computer program product of claim 47, wherein the second distribution pattern for assigning a second component includes electronic data identifying a fixed amount of the second component to be assigned to one or more cells in the arrangement.

49. The computer program product of claim 48, wherein the second distribution pattern for assigning a second component includes electronic data identifying a minimum and a maximum amount of the second component to be assigned to any of the cells of the arrangement and a second gradient to be applied between the minimum and maximum amounts of the second component across the cells.

50. The computer program product of claim 37, further comprising instructions operable to cause a programmable processor to generate a modified library design by receiving an input redefining a source, a destination or a mapping; recalculating the composition of one or more materials assigned to one or more of the cells; and generating a representation defining the modified library design.

51. The computer program product of claim 37, further comprising instructions operable to cause a programmable processor to:

receive an input defining one or more parameters, each parameter being electronic data corresponding to a process parameter to be applied to one or more cells of the arrangement and defining a parameter value for the one or more cells of the arrangement, the parameter value varying between a minimum and a maximum amount; and wherein the representation further comprises electronic data representing the one or more parameters.

52. The computer program product of claim 37, wherein the arrangement comprises two or more cells.

53. The computer program product of claim 37, wherein the arrangement comprises ten or more cells.

54. The computer program product of claim 37, wherein the arrangement comprises about ninety-six or more cells.

55. A computer program product on a computer-readable medium for generating a library design for a combinatorial library of materials, the computer program product comprising instructions operable to cause a programmable processor to:

receive an input defining a set of one or more sources and one or more destinations, each source being electronic data representing a component to be used in preparing the combinatorial library and each destination being electronic data representing an arrangement of cells;

receive an input defining a set of first mappings, the first mappings being electronic data defining a set of equations for calculating an amount of one or more components to be assigned to one or more cells in an arrangement;

use the set of equations to calculate a composition of a material assigned to one or more of the cells; and generate a representation of the library design, the representation comprising electronic data representing the sources, the destinations and the mappings.

56. The computer program product of claim 55, further comprising instructions operable to:

display a visual representation of the library design, the visual representation graphically describing the composition of one or more materials assigned to one or more of the cells.

57. The computer program product of claim 55, wherein the component to be assigned to a cell in the arrangement is determined by the location of the cell within the arrangement.

58. The computer program product of claim 57, wherein the composition of a material is determined using a subset of the set of equations, the subset of equations being determined by the location of the cell within the arrangement.

59. The computer program product of claim 55, further comprising instructions operable to:

generate an error indicator signal if the number of equations in the set of equations is not equal to the number of sources in the set of sources.

60. The computer program product of claim 55, wherein at least one of the set of equations is selected from the group consisting of:

a ratio equation defining an amount of a component to be assigned to a cell as a function of an amount of another component to be assigned to the cell;

a volume equation defining an amount of a component to be assigned to a cell as a function of a total volume of a plurality of components to be assigned to the cell; and a mass equation defining an amount of a component to be assigned to a cell as a function of a total mass of a plurality of components to be assigned to the cell.

61. The computer program product of claim 55, wherein the set of equations comprises a gradient equation defining an amount of a component to be assigned to each of a plurality of cells according to a gradient.

62. The computer program product of claim 55, wherein each of the set of equations is assigned to one or more cells of the arrangement according to the location of the cells within the arrangement.

63. The computer program product of claim 55, wherein the instructions operable to cause a programmable processor to use the set of equations to calculate a composition of a material assigned to one or more of the cells comprise instructions simultaneously to solve a set of interdependent equations.

64. The computer program product of claim 63, wherein the instructions simultaneously to solve the set of interdependent equations further comprise instructions to use a matrix inversion technique to solve the set of equations.

65. The computer program product of claim 55, further comprising instructions operable to:

receive an input defining a second mapping, the second mapping being electronic data defining a distribution pattern for distributing a component to cells in the arrangement, the distribution pattern including a minimum amount and a maximum amount of the component to be assigned to any cell of the cells of the arrangement and a gradient to be applied between the minimum and maximum amounts of the component across the plurality of cells; and use the first set of mappings and the second mapping to calculate a composition of a material assigned to one or more of the cells.

66. A computer program product on a computer-readable medium for generating a library design for a combinatorial library of materials, the computer program product comprising instructions operable to cause a programmable processor to:

receive an input defining a set of one or more sources and one or more destinations, each source being electronic data representing a component to be used in preparing the combinatorial library and each destination being electronic data representing an arrangement of cells;

receive an input defining a plurality of mappings, the mappings in the aggregate defining a composition for each of a plurality of materials assigned to a plurality of cells in the arrangement;

receive an input defining one or more parameters, each parameter being electronic data corresponding to a process parameter to be applied to one or more cells of the arrangement and defining a parameter value for the one or more cells of the arrangement, the parameter value varying between a minimum and a maximum amount; and generate a representation of the library design, the representation comprising electronic data describing the source elements, the destination elements, the mappings and the parameters.

67. The computer program product of claim 66, wherein the parameter value is defined to vary over time.

68. The computer program product of claim 66, wherein the parameter value is defined to vary across two or more cells in the arrangement.

69. The computer program product of claim 66, wherein the parameter value is defined to vary over time and across two or more cells in the arrangement.

70. The computer program product of claim 66, wherein the parameter value varies according to a gradient selected from the group consisting of linear, logarithmic, exponential, polynomial and geometric progression.

71. The computer program product of claim 66, wherein the parameter value corresponds to a process parameter selected from the group consisting of temperature, pressure, time, flow-rate and stirring speed.

72. A computer program product on a computer-readable medium for generating a library design for a combinatorial library of materials, the computer program product comprising instructions operable to cause a programmable processor to:

create a library design by defining a set of design elements, the set of design elements including one or more sources representing components to be used in preparing the combinatorial library, one or more destinations, each destination comprising an arrangement of one or more cells, and one or more elements selected from the group consisting of a mapping defining a scheme for assigning one or more amounts of a component to one or more cells of an arrangement and a parameter corresponding to a process parameter to be applied to one or more cells of the arrangement, the parameter defining a parameter value for the one or more cells of the arrangement, the parameter value varying between a minimum and a maximum amount;

generate a representation comprising electronic data describing the sources, the destinations, the mappings and the parameters; and use the representation to cause an automated material handling apparatus to assemble the combinatorial library on a substrate.

73. The method of claim 1, wherein:

each of the sources has an associated set of source properties describing the source; and defining the sources comprises receiving for each of the sources a set of values for one or more of the source properties associated with the source.

74. The method of claim 73, wherein:

at least one of the source properties is selected from the group consisting of molecular weight, equivalents, density and concentration.

75. The method of claim 73, wherein:

at least one of the source properties is a type describing a class of chemicals to be used in generating the library design.

76. The computer program product of claim 37, wherein:

each of the sources has an associated set of source properties describing the source; and the instructions operable to cause a programmable processor to define the sources include instructions operable to cause a programmable processor to receive for each of the sources a set of values for one or more of the source properties associated with the source.

77. The computer program product of claim 76, wherein:

at least one of the source properties is selected from the group consisting of molecular weight, equivalents, density and concentration.

78. The computer program product of claim 76, wherein:

at least one of the source properties is a type describing a class of chemicals to be used in generating the library design.

* * * * *

UNITED STATES PATENT AND TRADEMARK OFFICE
CERTIFICATE OF CORRECTION

PATENT NO. : 7,199,809 B1  Page 1 of 4
APPLICATION NO. : 09/420334
DATED : April 3, 2007
INVENTOR(S) : Lacy et al.

It is certified that error appears in the above-identified patent and that said Letters Patent is hereby corrected as shown below:

Beginning at Column 29, Line 15 through Column 36, Line 65, Claims 1 through 78 should be replaced with the following 16 claims:

1. A computer-implemented method for generating a library design for a combinatorial library of materials, comprising:
providing a graphical user interface including a workspace for designing a library of materials;
defining one or more sources and one or more destinations, each source being electronic data representing a chemical or mixture of chemicals to be used in preparing the combinatorial library and each destination being electronic data representing an arrangement of cells;
displaying a visual representation of one or more of the one or more defined destinations in the workspace of the graphical user interface, each destination representation including a representation of one or more destination areas, each destination area including one or more cells in the corresponding arrangement;
receiving user input associating each of the one or more sources with one or more of the destination areas;
receiving user input specifying a plurality of equations and associating each of the plurality of equations with one or more of the one or more destination areas;
solving the plurality of equations to calculate one or more amounts of one or more first chemicals or mixtures of chemicals represented by the one or more defined sources to be assigned to one or more cells in the one or more arrangements represented by the one or more defined destinations, the one or more amounts of the one or more first chemicals or mixtures of chemicals to be assigned to a given cell in the one or more arrangements being calculated according to a set of equations comprising a plurality of the equations, the equations in the set of equations being associated with the area or areas that include the cell, the one or more first chemicals or mixtures of chemicals to be assigned to the given cell being determined by the one or more sources associated with the area or areas that include the cell; and
modifying the visual representation of the one or more defined destinations to include a visual indication of the one or more calculated amounts.

Signed and Sealed this

Fifteenth Day of June, 2010

David J. Kappos
*Director of the United States Patent and Trademark Office*

2. The method of claim 1, further comprising:
generating an error indicator signal if the plurality of equations cannot be solved for each cell in the one or more arrangements.

3. The method of claim 1, wherein at least one of the plurality of equations is selected from the group consisting of:
a ratio equation defining an amount of one of the first chemicals or mixtures of chemicals to be assigned to a cell as a function of an amount of another chemical or mixture of chemicals to be assigned to the cell;
a volume equation defining an amount of one of the first chemicals or mixtures of chemicals to be assigned to a cell as a function of a total volume of a plurality of chemicals or mixtures of chemicals to be assigned to the cell; and
a mass equation defining an amount of one of the first chemicals or mixtures of chemicals to be assigned to a cell as a function of a total mass of a plurality of chemicals or mixtures of chemicals to be assigned to the cell.

4. The method of claim 1, wherein solving the plurality of equations comprises using matrix algebra techniques to solve the plurality of equations.

5. The method of claim 1, further comprising:
receiving an input defining a gradient mapping, the gradient mapping being electronic data defining a distribution pattern for distributing a second chemical or mixture of chemicals to cells in the one or more arrangements, the distribution pattern including a minimum and a maximum amount of the second chemical or mixture of chemicals to be assigned to any of a plurality of cells of the one or more arrangements and a gradient to be applied between the minimum and maximum amounts of the second chemical or mixture of chemicals across the plurality of cells; and
using the second mapping to calculate amounts of the second chemical or mixture of chemicals to be deposited in each of the plurality of cells;
wherein modifying the visual representation of the one or more defined destinations comprises modifying the visual representation to include a visual indication of the calculated amounts of the first and second chemicals or mixtures of chemicals.

6. A computer program product on a computer-readable medium for generating a library design for a combinatorial library of materials, the computer program product comprising instructions operable to cause a programmable processor to:
provide a graphical user interface including a workspace for designing a library of materials;
define a set of one or more sources and one or more destinations, each source being electronic data representing a chemical or mixture of chemicals to be used in preparing the combinatorial library and each destination being electronic data representing an arrangement of cells;
display a visual representation of one or more of the one or more defined destinations in the workspace of the graphical user interface, each destination representation including a representation of one or more destination areas, each destination area including one or more cells in the corresponding arrangement;
receive user input associating each of the one or more sources with one or more of the destination areas;
receive user input specifying a plurality of equations and associating each of the plurality of equations with one or more of the destination areas;

solve the plurality of equations to calculate one or more amounts of one or more first chemicals or mixtures of chemicals represented by the one or more defined sources to be assigned to one or more cells in the one or more arrangements represented by the one or more defined destinations, the one or more amounts of the one or more first chemicals or mixtures of chemicals to be assigned to a given cell in the one or more arrangements being calculated according to a set of equations comprising a plurality of the equations, the equations in the set of equations being associated with the area or areas that include the cell, the one or more first chemicals or mixtures of chemicals to be assigned to the given cell being determined by the one or more sources associated with the area or areas that include the cell; and modify the visual representation of the one or more defined destinations to include a visual indication of the one or more calculated amounts.

7. The computer program product of claim 6, further comprising instructions operable to:
generate an error indicator signal if the plurality of equations cannot be solved for each cell in the one or more arrangements.

8. The computer program product of claim 6, wherein at least one of the plurality of equations is selected from the group consisting of:
a ratio equation defining an amount of one of the first chemicals or mixtures of chemicals to be assigned to a cell as a function of an amount of another chemical or mixture of chemicals to be assigned to the cell;
a volume equation defining an amount of one of the first chemicals or mixtures of chemicals to be assigned to a cell as a function of a total volume of a plurality of chemicals or mixtures of chemicals to be assigned to the cell; and
a mass equation defining an amount of one of the first chemicals or mixtures of chemicals to be assigned to a cell as a function of a total mass of a plurality of chemicals or mixtures of chemicals to be assigned to the cell.

9. The computer program product of claim 6, wherein the instructions operable to cause a programmable processor to solve the plurality of equations comprise instructions to use matrix algebra techniques to solve the plurality of equations.

10. The computer program product of claim 6, further comprising instructions operable to:
receive an input defining a gradient mapping, the gradient mapping being electronic data defining a distribution pattern for distributing a second chemical or mixture of chemicals to cells in the one or more arrangements, the distribution pattern including a minimum and a maximum amount of the second chemical or mixture of chemicals to be assigned to any of a plurality of cells of the one or more arrangements and a gradient to be applied between the minimum and maximum amounts of the second chemical or mixture of chemicals across the plurality of cells; and
use the second mapping to calculate amounts of the second chemical or mixture of chemicals to be deposited in each of the plurality of cells;
wherein the instructions operable to cause a programmable processor to modify the visual representation of the one or more defined destinations include instructions operable to cause a programmable processor to modify the visual representation to include a visual indication of the calculated amounts of the first and second chemicals or mixtures of chemicals.

11. The method of claim 1, further comprising:
receiving user input dividing one or more of the one or more destination representations to define the destination areas.

12. The method of claim 1, further comprising:
in response to the user input specifying and associating the equations, modifying the visual representation of the one or more defined destinations to include a visual indication of the equations associated with the one or more destination areas.

13. The method of claim 1, wherein:
defining the one or more sources comprises associating one or more of the chemicals or mixtures of chemicals with a type representing a class of chemicals to be used in preparing the combinatorial library;
receiving user input specifying a plurality of equations comprises receiving user input specifying one or more of the plurality of equations as a function of the type; and
solving the equations comprises solving the equations specified as a function of the type for a given destination area by substituting the corresponding associated chemical or chemicals associated for the type.

14. The computer program product of claim 6, further comprising instructions operable to cause a programmable processor to:
receive user input dividing one or more of the destination representations to define the destination areas.

15. The computer program product of claim 6, further comprising instructions operable to cause a programmable processor to:
modify the visual representation of the one or more defined destinations in response to the user input specifying and associating the equations to include a visual indication of the equations associated with the one or more destination areas.

16. The computer program product of claim 6, wherein:
the instructions operable to cause a programmable processor to define the one or more sources comprise instructions operable to cause a programmable processor to associate one or more of the chemicals or mixtures of chemicals with a type representing a class of chemicals to be used in preparing the combinatorial library;
the instructions operable to cause a programmable processor to receive user input specifying a plurality of equations comprise instructions operable to cause a programmable processor to receive user input specifying one or more of the plurality of equations as a function of the type; and
instructions operable to cause a programmable processor to solve the equations comprise instructions operable to cause a programmable processor to solve the equations specified as a function of the type for a given destination area by substituting the corresponding associated chemical or chemicals associated for the type.